(12) United States Patent
Kezurer et al.

(10) Patent No.: US 11,478,226 B2
(45) Date of Patent: Oct. 25, 2022

(54) SYSTEM AND METHOD FOR ULTRASOUND ANALYSIS

(71) Applicants: New York University, New York, NY (US); Yeda Research And Development Co. Ltd, Rehovot (IL)

(72) Inventors: Itay Kezurer, Rehovot (IL); Achiau Ludomirsky, New York, NY (US); Yaron Lipman, Kibbutz Netzer Sereni (IL)

(73) Assignees: New York University, New York, NY (US); Yeda Research And Development Co., Ltd., Rehovot (IL)

( * ) Notice: Subject to any disclaimer, the term of this patent is extended or adjusted under 35 U.S.C. 154(b) by 135 days.

(21) Appl. No.: 16/478,507

(22) PCT Filed: Jan. 19, 2018

(86) PCT No.: PCT/US2018/014536
§ 371 (c)(1),
(2) Date: Jul. 17, 2019

(87) PCT Pub. No.: WO2018/136805
PCT Pub. Date: Jul. 26, 2018

(65) Prior Publication Data
US 2019/0388064 A1    Dec. 26, 2019

Related U.S. Application Data

(60) Provisional application No. 62/448,061, filed on Jan. 19, 2017.

(51) Int. Cl.
*A61B 8/08* (2006.01)
*G06N 3/08* (2006.01)
(Continued)

(52) U.S. Cl.
CPC ............ *A61B 8/5215* (2013.01); *A61B 8/488* (2013.01); *G06N 3/08* (2013.01); *G06N 20/00* (2019.01);
(Continued)

(58) Field of Classification Search
None
See application file for complete search history.

(56) References Cited

U.S. PATENT DOCUMENTS 6,106,466 A * 8/2000 Sheehan ............... A61B 5/1075
128/916
2005/0020903 A1 1/2005 Krishnan
(Continued)

FOREIGN PATENT DOCUMENTS

CN 106156793 11/2016
JP 2006509613 A 3/2006
(Continued)

OTHER PUBLICATIONS

International Search Report for corresponding PCT application PCT/US2018/014536 dated May 1, 2018.
(Continued)

*Primary Examiner* — Vikkram Bali
(74) *Attorney, Agent, or Firm* — Heidi Brun Associates Ltd.

(57) ABSTRACT

An exemplary system, method and computer-accessible medium for detecting an anomaly(ies) in an anatomical structure(s) of a patient(s) can be provided, which can include, for example, receiving imaging information related to the anatomical structure(s) of the patient(s), classifying a feature(s) of the anatomical structure(s) based on the imaging information using a neural network (s), and detecting the anomaly(ies) based on data generated using the classifica-
(Continued)

tion procedure. The imaging information can include at least three images of the anatomical structure(s).

16 Claims, 24 Drawing Sheets

(51) Int. Cl.
  *G06T 7/62* (2017.01)
  *G06T 7/194* (2017.01)
  *G06N 20/00* (2019.01)
  *G06T 7/00* (2017.01)
  *G06T 17/20* (2006.01)

(52) U.S. Cl.
  CPC ............ *G06T 7/0012* (2013.01); *G06T 7/194* (2017.01); *G06T 7/62* (2017.01); *G06T 17/20* (2013.01); *G06T 2207/10132* (2013.01); *G06T 2207/20081* (2013.01); *G06T 2207/20084* (2013.01)

(56) References Cited

U.S. PATENT DOCUMENTS

| | | | |
|---|---|---|---|
| 2005/0100208 A1 | 5/2005 | Suzuki et al. | |
| 2005/0147303 A1 | 7/2005 | Zhou | |
| 2006/0074315 A1 | 4/2006 | Liang et al. | |
| 2006/0159342 A1 | 7/2006 | Sun et al. | |
| 2008/0085050 A1 | 4/2008 | Barbu | |
| 2009/0074280 A1 | 3/2009 | Lu | |
| 2010/0240996 A1 | 9/2010 | Ionasec et al. | |
| 2011/0243401 A1 | 10/2011 | Zabair et al. | |
| 2014/0072213 A1 | 3/2014 | Paiton | |
| 2015/0112182 A1* | 4/2015 | Sharma | A61B 5/7264 600/408 |
| 2015/0112901 A1 | 4/2015 | Singer | |
| 2015/0366532 A1 | 12/2015 | Voigt et al. | |
| 2016/0174902 A1* | 6/2016 | Georgescu | G06T 7/0012 600/408 |
| 2019/0340470 A1* | 11/2019 | Hsieh | G06K 9/4604 |

FOREIGN PATENT DOCUMENTS

| | | |
|---|---|---|
| JP | 2009072593 A | 4/2009 |
| JP | 2011000462 A | 1/2011 |
| JP | 2016168332 A | 9/2016 |
| WO | 2004054443 A | 7/2004 |
| WO | 2005081168 | 9/2005 |

OTHER PUBLICATIONS

Supplementary European Search Report for corresponding European application 18741267.1 dated Jan. 7, 2020.
English Abstract of CN 106156793 downloaded from Google Patents on Feb. 13, 2020.
Ian Goodfellow, Jean Pouget-Abadie, Mehdi Mirza, Bing Xu, David Warde-Farley, Sherjil Ozair, Aaron Courville, and Yoshua Bengio, Generative adversarial nets, Advances in neural information processing systems, 2014, pp. 2672-2680.
Phillip Isola, Jun-Yan Zhu, Tinghui Zhou, and Alexei A Efros, Image-to-image translation with conditional adversarial networks, arXiv preprint arXiv:1611.07004 (2016).
Alex Krizhevsky, Ilya Sutskever, and Geoffrey E Hinton, Imagenet classification with deep convolutional neural networks, Advances in neural information processing systems, 2012, pp. 1097-1105.
First Examination Report issued in corresponding Indian application No. 201917033123, dated Sep. 15, 2021.
First Notice of Rejection issued in corresponding Japanese application No. 2019-539232, dated Sep. 21, 2021, together with machine English translation downloaded from Japan Patent Office.
Search Report issued in corresponding Russian application No. 2019125590, dated Sep. 18, 2021, together with English translation.

* cited by examiner

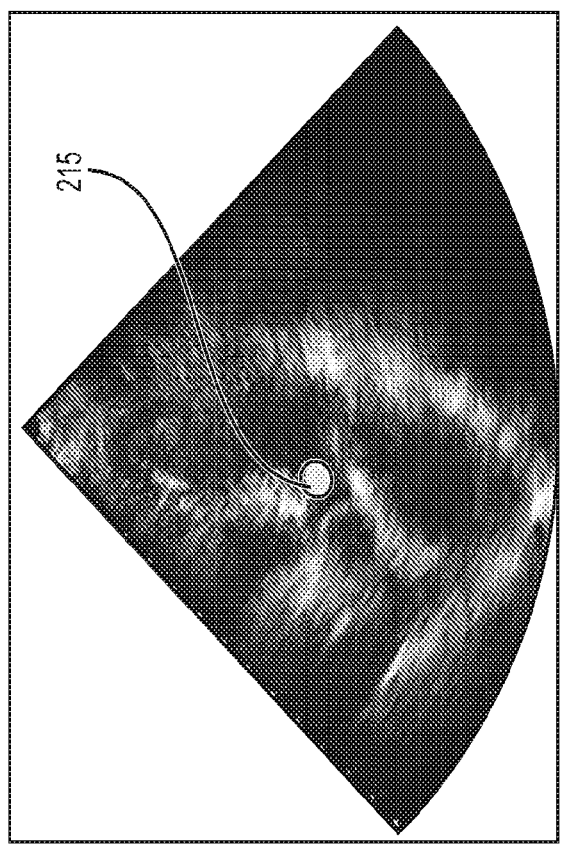
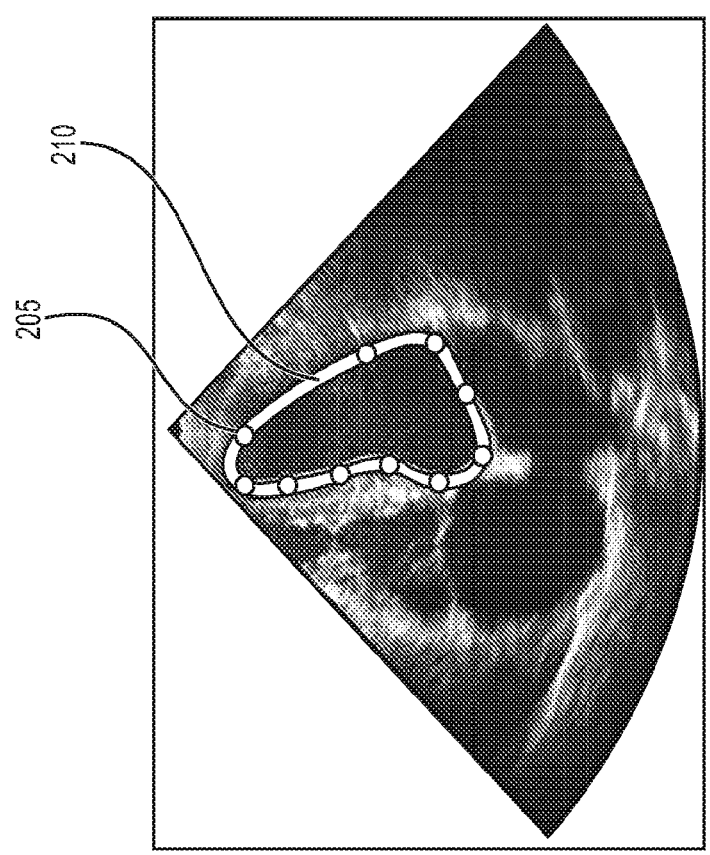
FIG. 2B
FIG. 2A

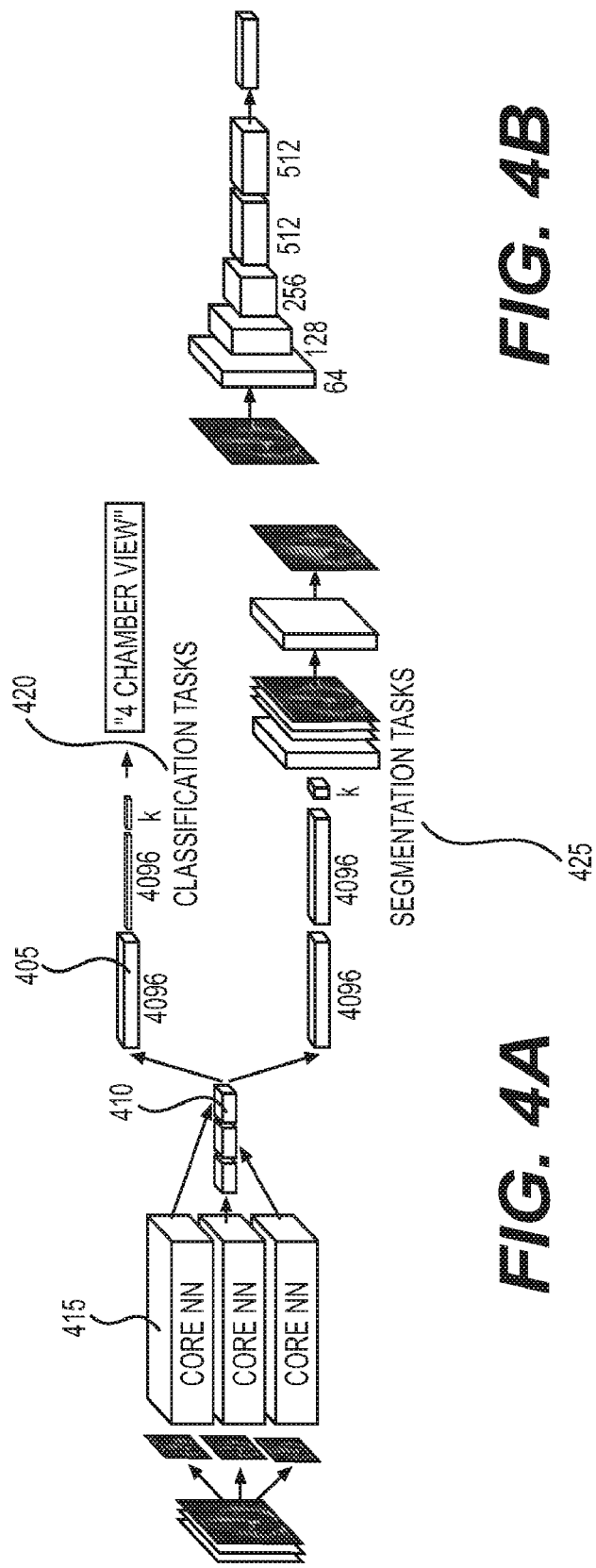

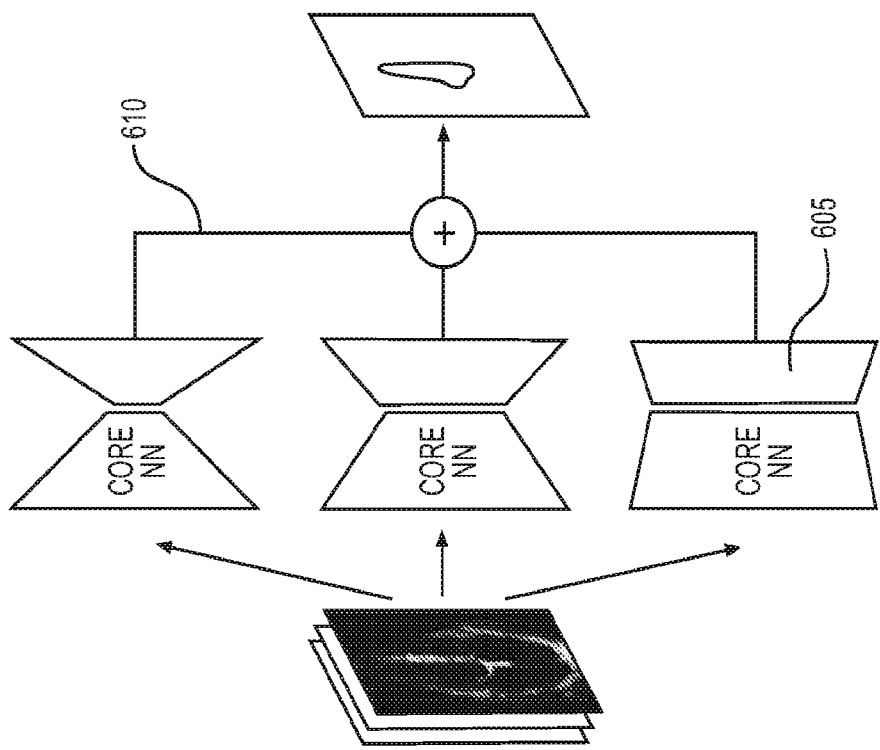
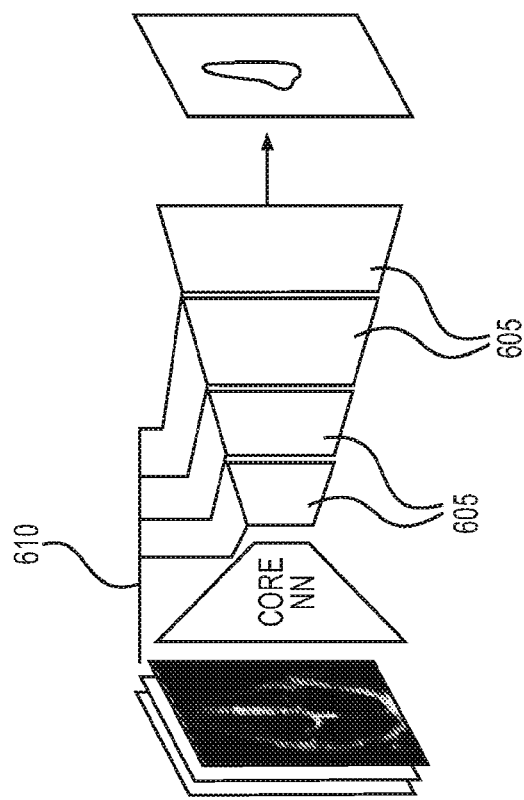
FIG. 6B
FIG. 6A

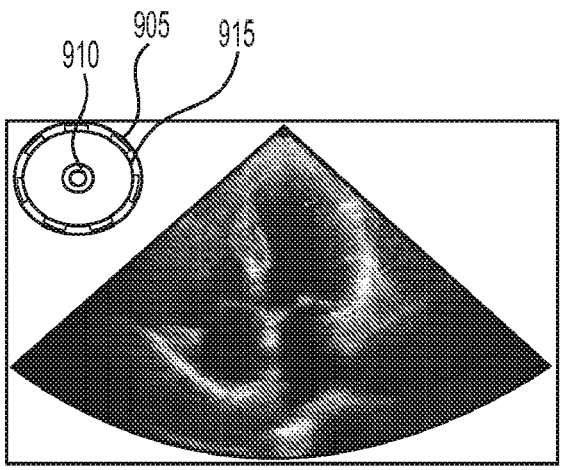
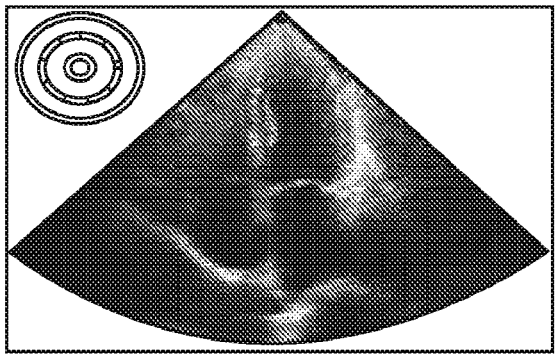
FIG. 9A    FIG. 9B
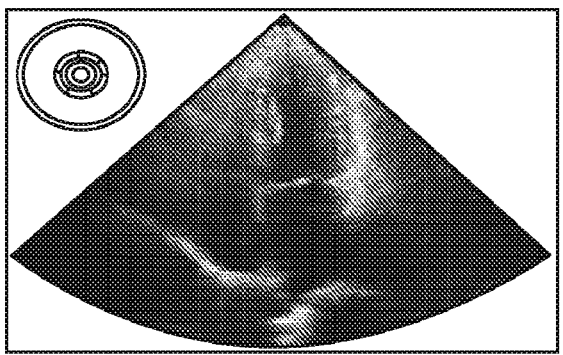
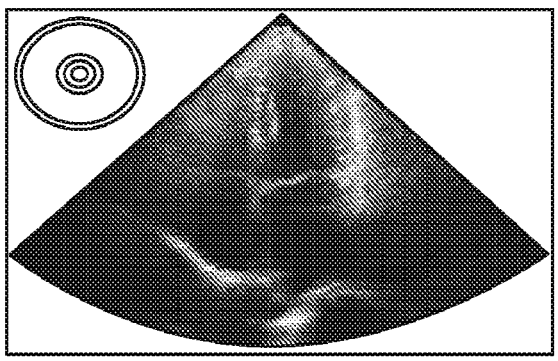
FIG. 9C    FIG. 9D
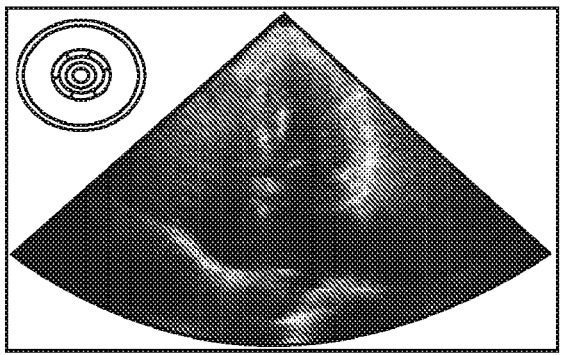
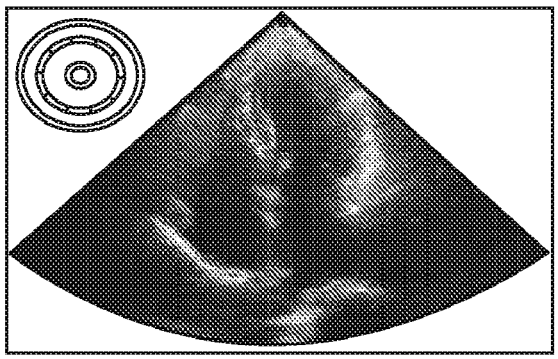
FIG. 9E    FIG. 9F

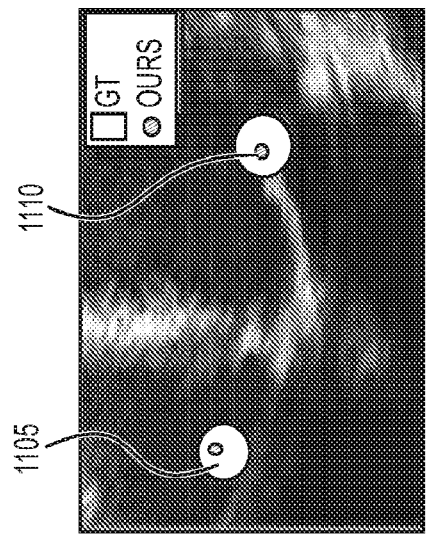
FIG. 11A
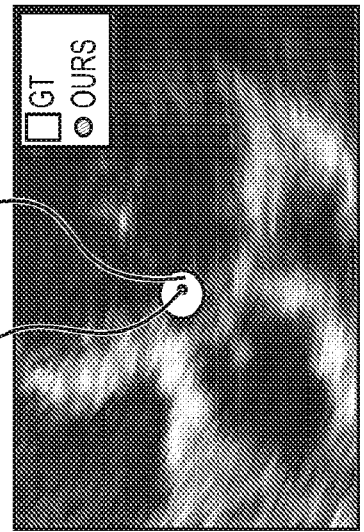
FIG. 11B
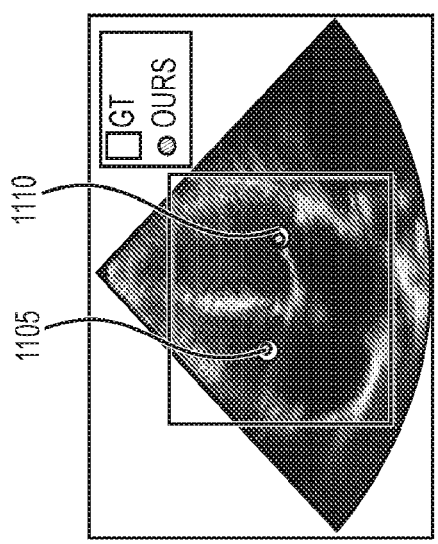
FIG. 11C
FIG. 11D

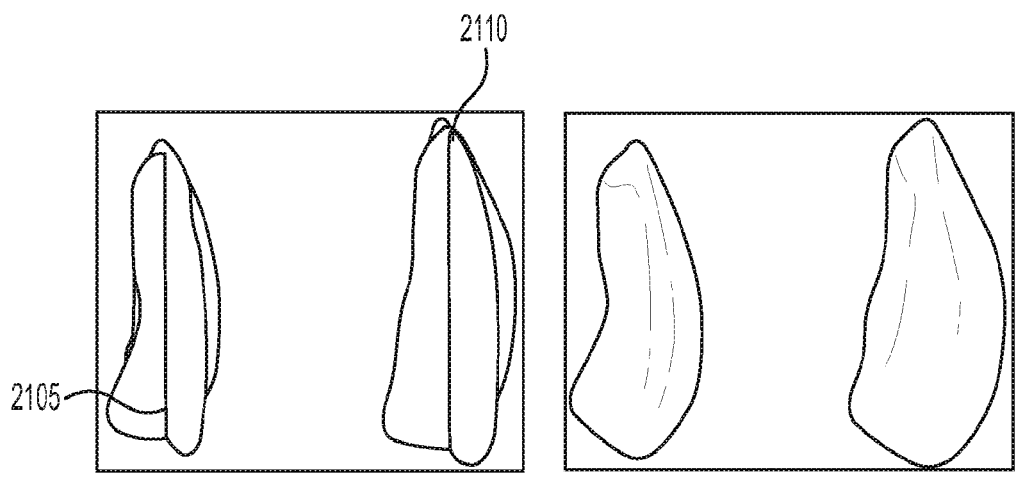
FIG. 21A  FIG. 21B
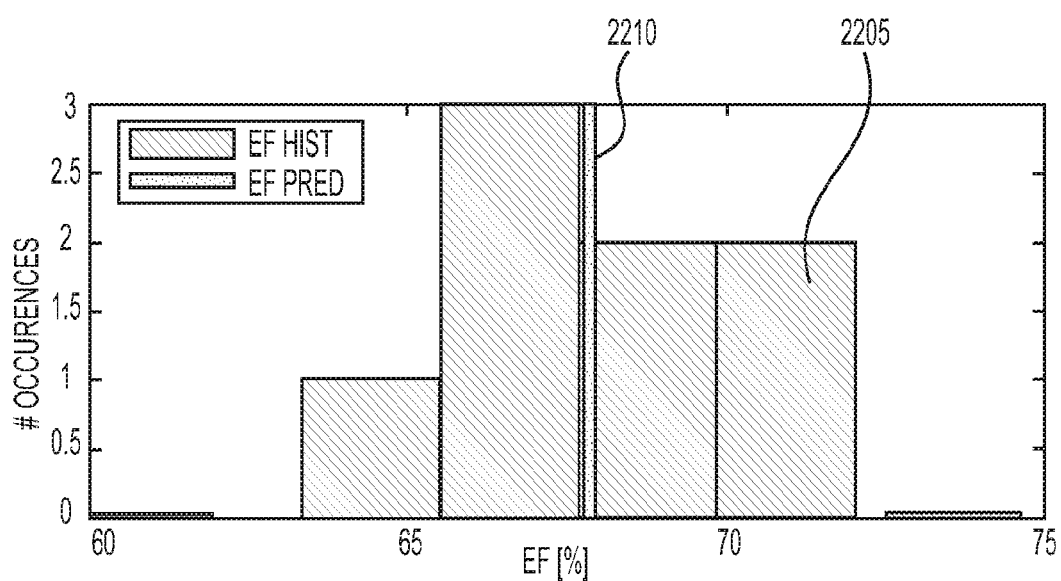
FIG. 22

SYSTEM AND METHOD FOR ULTRASOUND ANALYSIS

CROSS-REFERENCE TO RELATED APPLICATION(S)

This application is a national phase patent application of PCT patent application No. PCT/US2018/014536, filed Jan. 19, 2018, which relates to and claims priority from U.S. Patent Application No. 62/448,061, filed on Jan. 19, 2017, the entire disclosure of both of which are incorporated herein by reference.

FIELD OF THE DISCLOSURE

The present disclosure relates generally to use of an ultrasound apparatus, and more specifically, to exemplary embodiments of an exemplary system, method and computer-accessible medium for ultrasound analysis.

BACKGROUND INFORMATION

Echocardiogram, or ultrasound of the heart, is a common clinical tool for assessing a heart condition, and for identifying and diagnosing certain heart diseases. Currently, a significant amount of the analysis and processing of the input ultrasound movie clips is performed by a technician or a physician ("user"). Such manual analysis has several drawbacks, for example: (i) it increases the chance of error, (ii) it needs a skilled user, (iii) it limits the throughput by the analyzing speed and skill of the user and (iv) due to time complexity, only several frames from the clips are fully analyzed while information in other frames is left unused.

Cardiac ultrasound can be the preferred modality for the assessment of cardiac anatomy, function and structural anomalies. Currently, routine cardiac ultrasound examination lasts between about 30 and about 40 minutes, and can include: (i) acquisition of the data by ultrasound and Doppler procedures, (ii) analysis of ventricular function and multiple measurements of the different parts of the cardiac structure, and (iii) a report that can be incorporated directly in the electronic medical record.

Thus, it may be beneficial to provide an exemplary system, method and computer-accessible medium for ultrasound analysis, and which can overcome at least some of the deficiencies described herein above.

SUMMARY OF EXEMPLARY EMBODIMENTS

An exemplary system, method and computer-accessible medium for detecting an anomaly(ies) in an anatomical structure(s) of a patient(s) can be provided, which can include, for example, receiving imaging information related to the anatomical structure(s) of the patient(s), classifying a feature(s) of the anatomical structure(s) based on the imaging information using a neural network(s), and detecting the anomaly(ies) based on data generated using the classification procedure. The imaging information can include at least three images of the anatomical structure(s).

In some exemplary embodiments of the present disclosure, the imaging information can include ultrasound imaging information. The ultrasound imaging information can be generated using, e.g., an ultrasound arrangement. The anatomical structure(s) can be a heart. In certain exemplary embodiments of the present disclosure, the state(s) of the anatomical structure(s) can include (i) a systole state of a heart of the patient(s), (ii) a diastole state of the heart of the patient(s), (iii) an inflation state of the heart of the patient(s) or (iv) a deflation state of the heart of the patient(s).

In some exemplary embodiments of the present disclosure, the feature(s) can be classified using a view detection procedure, which can include detecting a view of a particular imaging frame in the imaging information. The anatomical structure(s) can be segmented, e.g., using a part segmentation procedure and a localization procedure before the detection of the anomaly(ies). The part segmentation procedure can be utilized to segment a left ventricle of the heart of the patient(s) from a background. The localization procedure can be a valve localization procedure, which can include marking, a single pixel per frame in the imaging information to place a Doppler measuring point(s).

In certain exemplary embodiments of the present disclosure, the imaging information can include a plurality of images, and neural network(s) can include a plurality of neural networks each one of which can be associated with one of the images. Each neural network can be used to classify the feature(s) in its associated one of the images. An output produced by each of the neural networks can be concatenated (e.g., in a depth). The imaging information can be upsampled.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 2A is an exemplary image of the acquisition of labels for segmentation according to an exemplary embodiment of the present disclosure;

FIG. 2B is an exemplary image of labels for valve localization according to an exemplary embodiment of the present disclosure;

FIG. 4A is an exemplary diagram of network architecture used by the exemplary system according to an exemplary embodiment of the present disclosure;

FIG. 4B is an exemplary diagram of a Core Neural Network according to an exemplary embodiment of the present disclosure;

FIGS. 6A and 6B are exemplary diagrams of the exemplary system, method and computer-accessible medium according to an exemplary embodiment of the present disclosure;

FIGS. 9A-9F are exemplary images of the per-frame stages in the cardiac cycle according to an exemplary embodiment of the present disclosure;

FIGS. 11A and 11C are exemplary images of valve localization performed using the exemplary system according to an exemplary embodiment of the present disclosure;

FIGS. 11B and 11D are exemplary magnified images of the valve localization images of FIGS. 11A and 11C, respectively, according to an exemplary embodiment of the present disclosure;

FIG. 21A is a set of exemplary images of cross-sections of systole LV and diastole LV according to an exemplary embodiment of the present disclosure;

FIG. 21B is a set of exemplary images of the reconstructions of the 3D surface in systole and diastole according to an exemplary embodiment of the present disclosure;

FIG. 22 is an exemplary histogram generated using the exemplary system, method and computer-accessible medium according to an exemplary embodiment of the present disclosure;

Figure 1:
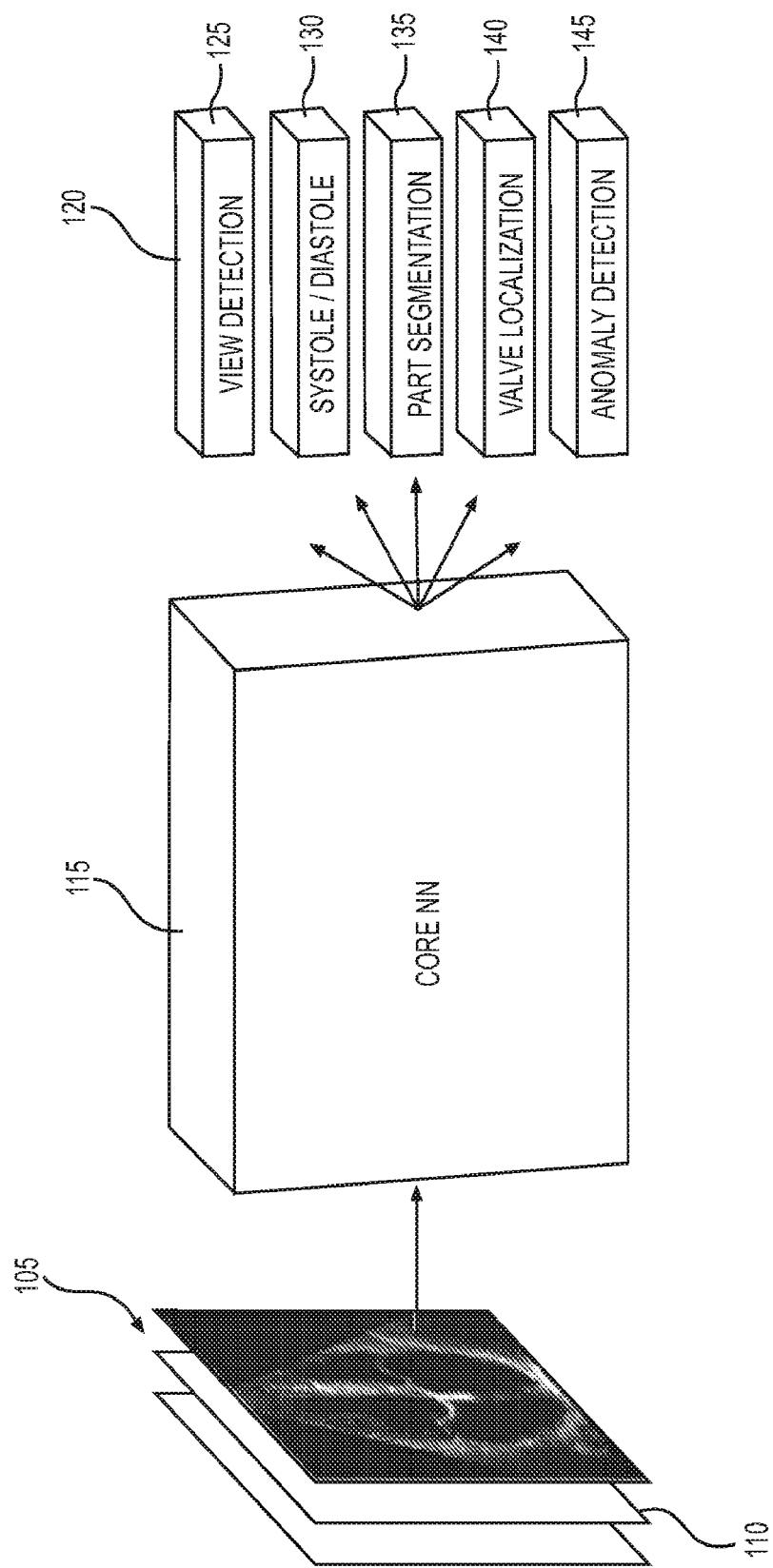
FIG. 1 is an exemplary diagram of an exemplary ultrasound analysis system according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary embodiments of the present disclosure may be further understood with reference to the following description and the related appended drawings. The exemplary embodiments are described with reference to cardiovascular imaging (e.g., using ultrasound). However, those having ordinary skill in the art will understand that the exemplary embodiments of the present disclosure may be implemented for imaging other tissues or organs (e.g., other than the heart) and can be used in other imaging modalities (e.g., other than ultrasound, including but not limited to MRI, CT, OCT, OFDR, etc.).

The exemplary system, method and computer-accessible medium, according to an exemplary embodiment of the present disclosure, can include a neural network core that can aid a healthcare provider in diagnosing and making clinical decisions more accurately, be of better quality, and have increased safety. For example, the exemplary neural network core can receive images from multiple imaging modalities including ultrasound, magnetic resonance imaging, positron emission scanners, computer tomography and nuclear scanners. The exemplary neural network core can be used for the examination of multiple organs, and is not limited to a specific organ system. The exemplary system, method and computer-accessible medium, according to an exemplary embodiment of the present disclosure, can be incorporated into, or connected to, online and/or offline medical diagnostic devices, thus facilitating the operator to become more accurate and efficient.

As shown in the diagram of FIG. 1, the exemplary system, method and computer-accessible medium, according to an exemplary embodiment of the present disclosure, can include a Core Neural-Network ("NN") 115. The Core NN 115 can take as input a sequence of ultrasound frames 105, and produce high-level semantic features for the middle frame 110 in the sequence. These exemplary semantic features can be used to solve a series of recognition and analysis procedures (e.g., element 120). For each exemplary procedure, a dedicated NN-based component can be built on top of the Core NN 115, and can be tailored specifically for that procedure. The exemplary procedures can be broken down into, for example, five exemplary groups: (i) View detection 125, (ii) Systole/diastole detection 130, (iii) Part segmentation 135, (iv) Valve localization 140 and (v) Anomaly detection 145. The procedures can be sorted according to their difficulty level (e.g., from easy to hard).

The first exemplary procedure (e.g., View detection 125) can be performed to detect the view of a given frame out of several potential views. The views currently handled can be ones used in a standard adult echocardiogram examination: (i) apical 2-chamber view, (ii) apical 3-chamber view, (iii) apical 4-chamber view, (iv) apical 5-chamber view, (v) parasternal long axis view and (vi) parasternal short axis view. The second exemplary procedure (e.g., Systole/diastole 130) can be performed to identify the systole/diastole in the cardiac cycle. For example, each frame can be labeled using one of the four temporal states of the left ventricle: (i) diastole, (ii) systole, (iii) inflating and (iv) deflating. The third exemplary procedure (e.g., Part segmentation 135) can be performed to segment regions in ultrasound images such as the four chambers of the heart, the heart valves and walls, and the pericardium. The fourth exemplary procedure (e.g., Valve localization 140) can be performed to identify the locations of valves for Doppler analysis of in/out flow through these valves. The fifth exemplary procedure (e.g., Anomaly detection 145) can be performed to detect and locate heart anomalies, such as pericardial effusion.

An exemplary observation can be that the Core NN that extracts high-level semantic features from a sequence of ultrasound images can be the same for all the procedures, and the exemplary system, method and computer-accessible medium, according to an exemplary embodiment of the present disclosure, can be trained by optimizing (e.g., simultaneously) all procedures and the Core NN. This exemplary approach can provide the following benefits. First, building an ultrasound feature system that can be trained and used for different complementary procedures can provide versatile features that can corroborate and improve individual procedure performance. The intuition can be similar to human learning; for example, to better detect the view of an ultrasound image, it can be beneficial to detect and segment the different visible parts of the heart, and vice-versa. Second, having a versatile feature system captured by the Core NN, an ultrasound analysis procedure can be added with rather low amounts of data. This can be because the main part of the exemplary system, the Core NN, can already be trained to produce generic features, and all that can be left to train can be the procedure specific part. This can facilitate adaptation of the exemplary system, method, and computer-accessible medium to new or different procedures with rather low computational complexity and time. Third, since it can usually be more difficult to achieve and/or produce data for the more difficult procedures, starting by training the system, method, and computer-accessible medium on the easier procedures provides a good starting point for more elaborate procedures.

The echocardiogram can often be used to extract high level quantitative information regarding the heart condition and function. An exemplary archetypical example is the Ejection Fraction ("EF"). The EF can be computed from various exemplary measurements including and combining view detection, systole/diastole detection, and part segmentation. The exemplary system, method and computer-accessible medium can utilize an automatic pipeline for determining the EF, including producing a 3D surface reconstruction of the LV, or other parts using the UT data (e.g., only the UT data).

Exemplary Data Generation

The exemplary system, method and computer-accessible medium, according to an exemplary embodiment of the present disclosure, can include the creation of data. An exemplary database consisting of 3000 ultrasound clips (e.g., approximately 40 frames each) was used. Each ultrasound frame $X_i$ was an n×n gray-scale image. The database was divided into three disjoint sets: (i) training, (ii) validation and (iii) test data.

An exemplary input to the exemplary system can include sequences (e.g., triplets) of consecutive ultrasound frames (e.g., l=3). Additionally, $X_i=(x_{i-d}, x_i, x_{i+d})$ (e.g., element 105 from FIG. 1), where d can be a parameter which can be set to d=1. The prediction performed by the exemplary system, method and computer-accessible medium, can be done with respect to the middle frame 110 (e.g., $x_i$). The input sequence of images can provide the system with a temporal context together with a spatial context.

The exemplary system, method and computer-accessible medium, according to an exemplary embodiment of the present disclosure, can support two types of procedures: (i) classification and (ii) segmentation. For each exemplary procedure, a ground-truth label $y_j$ was generated for a subset of the ultrasound frames $x_j$ in the exemplary database; $y_j$ can either be a single label (e.g., for classification procedures) or can consist of a label for each pixel in $x_j$ (e.g., for segmentation procedures). Thus, either $y_j \in \mathcal{L} = \{l_1, l_2, \ldots, l_k\}$ can be a single label, or $y_j \in \mathcal{L}^{n \times n}$ can be a per-pixel label (e.g., corresponding to each pixel of $x_j$).

The first two exemplary procedures can be classification procedures. For the first exemplary procedure of View detection, $y_j \in \mathcal{L}$ where $\mathcal{L} = \{SA, LA, 5C, 4C, 3C, 2C\}$ can correspond to Short-Axis, Long-Axis, 5 Chamber, 4 Chamber, 3 Chamber, and 2 Chamber views. For the procedure of Diastole/systole detection, $\mathcal{L} = \{DI, SY, IN, DE\}$, can correspond to DIastole, SYstole, INflating, and DEflating of the left ventricle. Since DI and SY can be instantaneous configurations, only two labels $\mathcal{L} = \{IN, DE\}$ were utilized, and these labels were assigned to all frames between peaks (e.g., strictly between diastole and systole and systole and diastole).

The next three exemplary procedures can be segmentation procedures. The exemplary part segmentation procedure implemented can use labels $y_j \in \mathcal{L}^{n \times n}$ where $\mathcal{L} = \{LV, BA\}$, LV can stand for Left-Ventricle and BA for Background. Given an input sequence of frames $X_i$ the exemplary goal can be to decide, for each pixel in the middle frame $x_i$, if it can be part of the left-ventricle or not. Manually labeling each pixel in $x_i$, can be tedious and impractical. Therefore, an exemplary software tool that can facilitate the generation of labels $y_j$ for a collection of frames $x_j$ as produced can be used. An exemplary screenshot from a labeling session is shown in the image in FIG. 2A. The user uses an interactive tool that can facilitate him/her to mark a sparse set of control points 205 and a smooth closed curve 210 (e.g., cubic spline) can be computed interpolating these points. The user can add, remove or edit these control points 205. The user can mark consecutive frames, and can use a previous frame's curve as an initialization. Given a closed curve drawn on a frame $x_j$, all the pixels within the region bounded by this curve can be marked with the same label $l_i \in \mathcal{L}$. For example, as shown in the image in FIG. 3A, the label $y_j$ corresponding to the frame $x_j$ in the image in FIG. 2A is shown, where white area 305 corresponds to the LV label and black area 310 to the BA label.

Figure 3B:
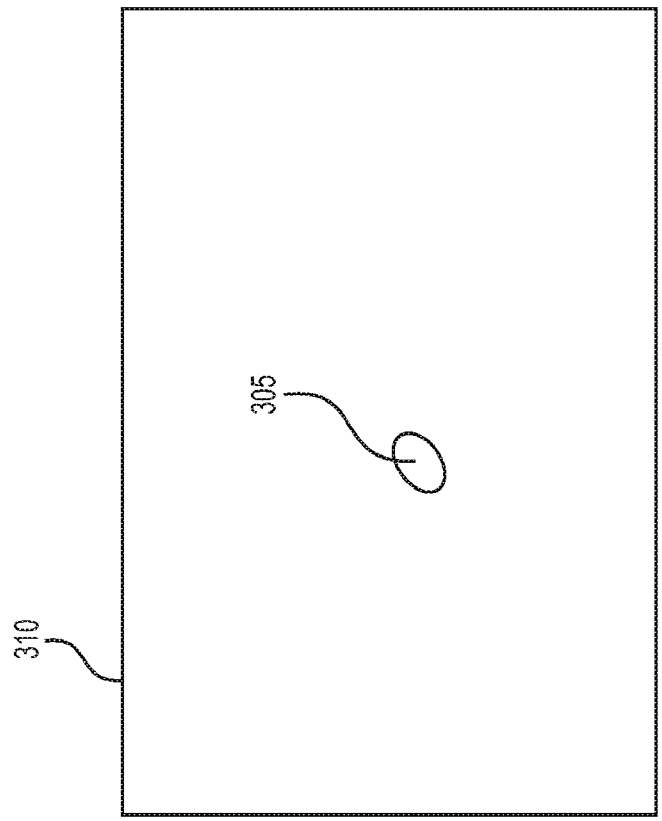
FIG. 3B is an exemplary image of data $\mathcal{Y}_j$ for valve localization according to an exemplary embodiment of the present disclosure.
Figure 3A:
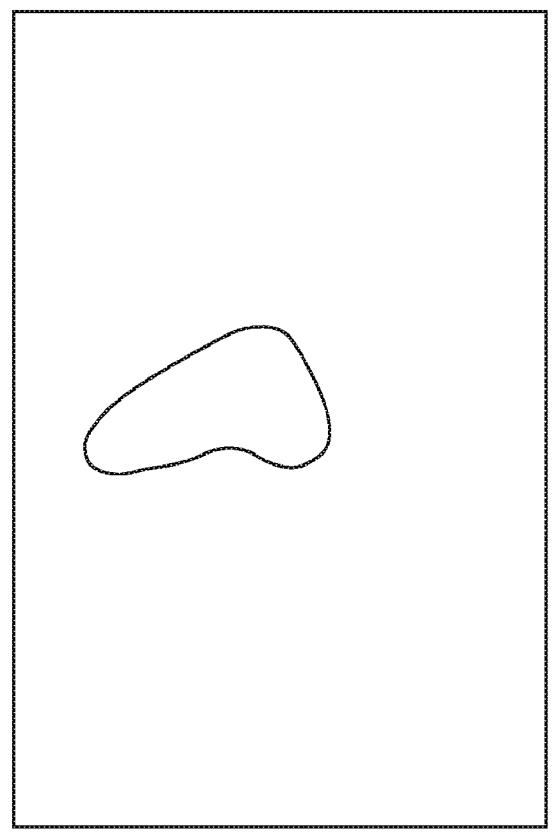
FIG. 3A is an exemplary image of data $\mathcal{Y}_j$ for part segmentation according to an exemplary embodiment of the present disclosure.

The exemplary Valve Localization procedure can utilize marking a single pixel per frame to place the Doppler measuring point. Three valves were implemented; $\mathcal{L} = \{MI, TR, AO, BA\}$, Mitral ("MI"), Tricuspidal ("TR"), Aortic ("AO") and background ("BA"). To generate data, an exemplary software tool, similar to the one used for part segmentation, was produced, which can facilitate the user to select a pixel in each image to indicate the location of the relevant valve. (See, e.g., FIG. 2B, element 215). To create meaningful training data, statistics were obtained by asking the user to mark the same set of 8 clips (e.g., 4 clips for 4C and 4 clips for 5C) 10 times. This data was used to calculate statistics of the valve sampling, and created the training data by splatting an ellipse centered at the user prescribed pixel with variances taken from the above statistics. This was performed separately and independently for each valve. For example, the image shown in FIG. 3B illustrates the label $y_j$ created for the frame shown in the image shown in FIG. 2B, where white pixels 305 represent the label AO, and black pixels 310 represent label BA.

In the exemplary anomaly detection, pericardial effusion and detect fluid accumulation in the pericardial cavity can be taken care of. In this exemplary segmentation procedure, the labels can discriminate pericardial fluid and background, $\mathcal{L} = \{PE, BA\}$. Similar software to the previous two segmentation procedures was built where the user can annotate the fluid areas.

Exemplary Network Architecture

FIG. 4A shows an exemplary diagram/architecture of the exemplary system, method and computer-accessible medium, according to an exemplary embodiment of the present disclosure. For example, as shown in FIG. 4A, each gray block 405 can represent a convolutional block that can consist of a series of convolutions and ReLU (e.g., activation) layers. For each convolutional block 405, the number of channels (e.g., depth) is indicated. Consecutive convolutional blocks 405, with different resolutions (e.g., width and height of blocks), can be connected by pooling layers. Blocks 410 can represent the output of the exemplary Core NN. The exemplary Core NN block 415 is shown in FIG. 4B; the architecture of Core NN 415 is shown in FIG. 4B. The input to the exemplary system can be a sequence of ultrasound frames $X_i = (x_{i-1}, x_i, x_{i+1})$; the system can feed each frame $x_{i-1}, x_i, x_{i+1}$ independently through the Core NN to achieve the high-level ultrasound features and can concatenate the output. The exemplary system, method and computer-accessible medium, according to an exemplary embodiment of the present disclosure, can use the concatenated features to perform the procedures described above.

The exemplary procedures can be divided into two groups: (i) classification procedures, and (ii) segmentation procedures. The exemplary classification procedure can request to assign a label $z_i \in \mathcal{L}$ from a set of possible labels $\mathcal{L} = \{l_1, \ldots, l_k\}$ for an input sequence $X_i$. The exemplary classification procedure can include View detection and Systole/diastole detection. The exemplary segmentation procedure can ask for a given input sequence $X_i$ to generate a label per-pixel for the middle frame $x_i$, that can be $\mathcal{Z}_i \in \mathcal{L}^{n \times n}$, where $x_i$ can be n×n image, and as before $\mathcal{L} = \{l_1, \ldots, l_k\}$. The exemplary segmentation procedure can include part segmentation, valve localization and anomaly detection. An anomaly detection can also have instantiation as a classification procedure. Each procedure can have its own network with suitable architecture based on its type (e.g., classification of segmentation).

The two groups of the exemplary procedures can use the same concatenated features produced by the exemplary Core NN. The exemplary classification procedures can use an exemplary classification framework (e.g., element 420 shown in FIG. 4A) (see, e.g., Reference 3), which can utilize fully connected layers to reduce the output to prediction vector in $\mathbb{R}^k$ (e.g., $k$ can be the number of classes in $\mathcal{L}$) from which a prediction $z_i$ can be made.

During the exemplary segmentation (see, e.g., element 425 shown in FIG. 4A), an exemplary up sampling procedure can be used, which can be different from existing semantic segmentation architectures (see, e.g., Reference 2), which can learn a deconvolution operator and inject previous layers; the low resolution can be up sampled to full resolution, and the output can be concatenated with the input sequence $X_i$, which can pass through a convolutional block to produce the final segmentation. The upsampled segmentation information can provide a smooth rough approximation of the part to be segmented, and the final convolutional block can use local features to refine its boundary.

The exemplary segmentation of a particular part/section of the heart, for example, the left-ventricle, can include a multi-scale task. For example, a rough estimate of the part location in the image can be provided, and the exemplary prediction can be gradually refined, or modified, based on local features of the image. The exemplary system, method and computer-accessible medium, according to an exemplary embodiment of the present disclosure, can include two exemplary architectures for segmenting anatomical parts from medical images. (See e.g., diagrams shown in FIGS. 6A and 6B).

For example, the diagram shown in FIG. 6A illustrates a first exemplary network in a serial form. This exemplary network can produce a bottom-up segmentation using consecutive upsampling blocks (element 605 shown in the diagram of FIG. 6A). Each block can include a bilinear or deconvolution up-sampling, and various convolutional-relu layers. Each block 605 can receive as an input the previous low-resolution segmentation, add to it a downsampled version of the original image data (e.g., lines 610), and can produce the segmentation in a higher resolution. One of the exemplary layers can produce the result in the resolution of the original image. FIG. 6B shows a diagram of an exemplary network in a parallel form. Truncated copies of the Core NN can be utilized, and attached to each an up-sampling block (e.g., similar to the serial design). Each truncated copy of the Core NN can be used to reduce the original images to different resolutions with corresponding receptive fields. For example, the lowest resolution can be used to recognize where the LV is but may not precisely determine the borders, while the highest resolution (e.g., the one with the smallest receptive field) can attempt to influence the borders of the segmentation based on local information in the image. The results can then be aggregated to achieve the final segmentation. It can also be possible to train the truncated Core NN for every resolution.

The exemplary system, method and computer-accessible medium, according to an exemplary embodiment of the present disclosure, can also consider the addition of a total variation regularizer directly to the network loss function in order to encourage segmentation with a shorter boundary curve. The total variation energy can be defined directly on the output of the segmentation network as $\lambda \Sigma_p \|([\nabla F(X_i)]_p)\|_2$, where F(X) can be the difference of the network response for a certain label (e.g., LV) and the background label BA when applied to the input sequence $X_i$, the sum can be over all pixels p, and $\lambda$ can be the amount of regularization.

The exemplary Core NN 415 illustrated in FIG. 4A can include an imagenet architecture (see, e.g., Reference 3), which can reduce an input image to a set of feature vectors defined on a very coarse resolution. In the exemplary system, the same Core NN can be used for transforming each of the input ultrasound frames $x_{i-1}$, $x_i$, $x_{i+1}$ to its feature vectors. The weights defining the exemplary Core NN can be coupled between its three realizations in the system. (See, e.g., multiple blocks 415 the exemplary Core NN).

The exemplary system and method, according to an exemplary embodiment of the present disclosure, can be utilized to improve the segmentation involve $L_1$ cost functions and Generative Adversarial Networks. For example, L1 regularization for segmentation can be used as a loss function, and can provide a more accurate boundary detection than standard crossentropy loss. Alternatively or in addition, an exemplary loss function can be trained using, for example, GANs. As an example, given some segmentation network, a discriminator network can be trained to distinguish real segmentations and segmentations created by the segmentation network. This discriminator, in combination with some other loss or on its own to further train the segmentation network, can be used. The input to the discriminator network can include (Xi, Zi) for real examples, and (Xi, f (Xi)), where f (Xi) can be the output of the segmentation network.

Exemplary Training

For training the exemplary system, an interleaving approach can be employed. For example, the first exemplary procedure (e.g., view detection) can be used, which can train its NN (see, e.g., element 420 shown in FIG. 4A) while fixing the Core NN. Both the Core NN and view-procedure NN can be trained. The second NN procedure (e.g., Diastole/systole) can be trained while fixing the Core NN followed by training both the Core NN and the Diastole/Systole-NN. This can be repeated/continued until a convergence is achieved. Since preliminary procedures can be easier to generate data for, training the Core NN on these applications already provides a good starting point for more challenging procedures. Alternatively or in addition, the exemplary system, method and computer-accessible medium, according to an exemplary embodiment of the present disclosure, can be utilized to train all exemplary tasks simultaneously.

Exemplary Evaluation

The exemplary system, method and computer-accessible medium, according to an exemplary embodiment of the present disclosure, was evaluated on test data that has not been used or validated in the training phase; the test data consisted of 322 clips (e.g., 10000 frames) for classification procedures, 42 clips (e.g., 530 frames) for part segmentation procedures and 108 clips (e.g., 2250 frames) for the Valve localization procedures.

Exemplary Performance

Exemplary View Detection

Figure 5:
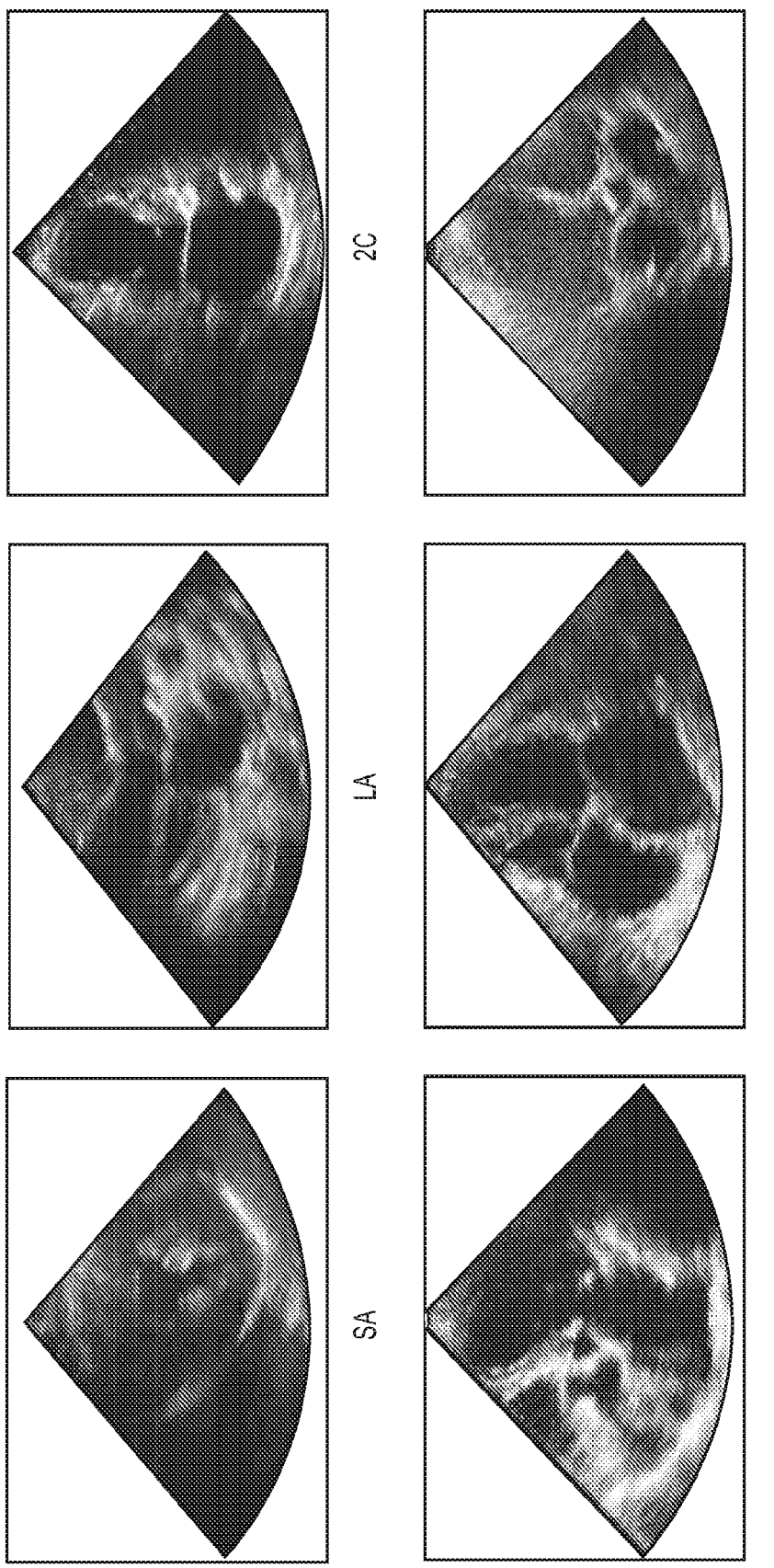
FIG. 5 is a set of exemplary images of different ultrasound views of the heart and their corresponding labels according to an exemplary embodiment of the present disclosure.
Figure 7A:
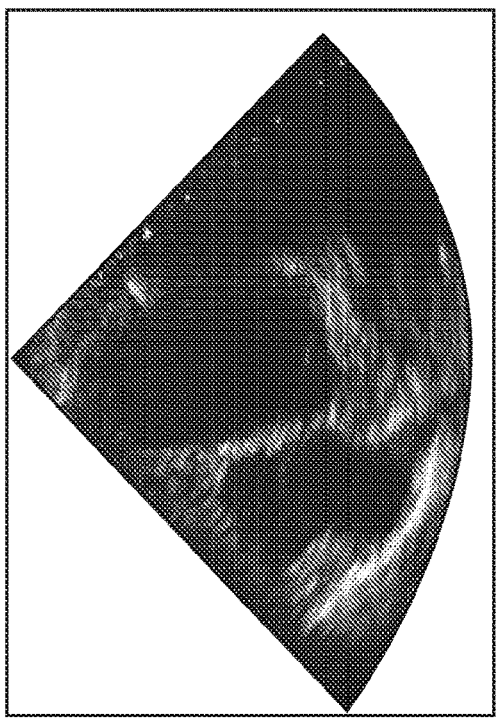
FIGS. 7A and 7B are exemplary images of the per-view probability generated by the exemplary system, method, and computer-accessible medium for two input triplet images according to an exemplary embodiment of the present disclosure.
Figure 7B:
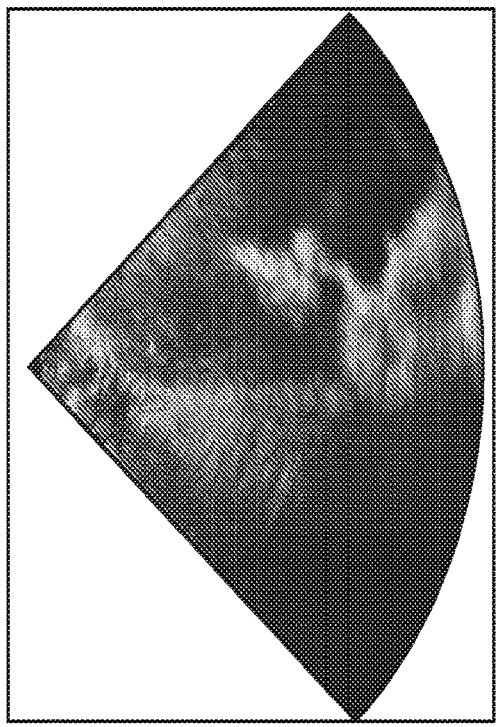
Figure 7C:
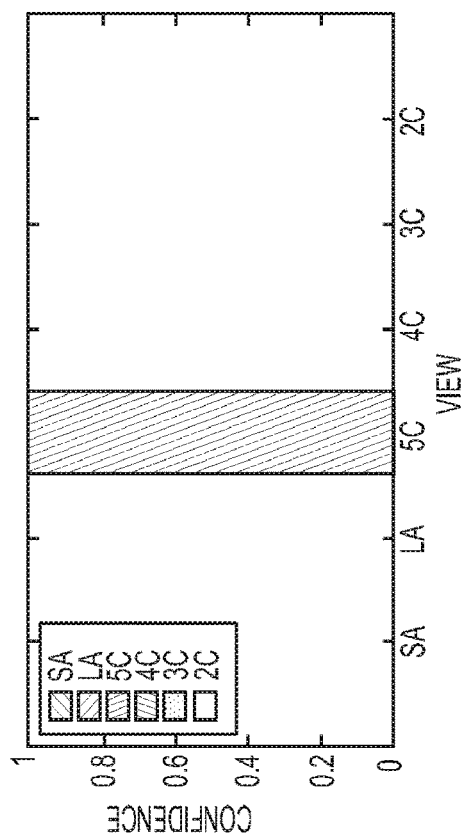
FIGS. 7C and 7D are exemplary histogram diagrams corresponding to FIGS. 6A and 6B, respectively, according to an exemplary embodiment of the present disclosure.
Figure 7D:
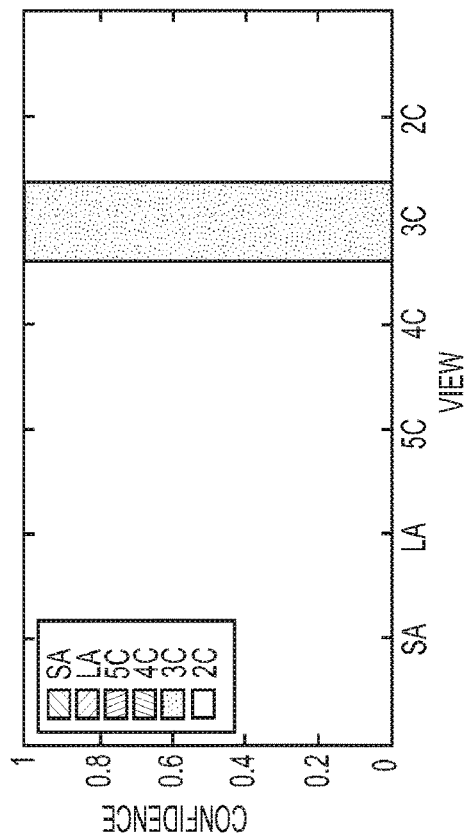

The view of a given frame $x_i$ can be used for the exemplary classification. For example, FIG. 5 shows an exemplary image from each view in the exemplary dataset. In this experiment, the label produced by the system was compared to the ground-truth label produced by the user. The system generated probabilities on the set of labels, and the view which received the highest probability was chosen as the system output. FIGS. 7A and 7B show images of the probabilities produced by the exemplary system, method and computer-accessible medium for two exemplary images; note the high confidence in the correct view label. The corresponding exemplary histograms are shown in FIGS. 7C and 7D, respectively. The output of the exemplary system, method and computer-accessible medium also compared to the ground-truth labeled views on the entire test data (e.g., 10 k frames) and produced correct view identification in 98.5% of the frames.

Exemplary Diastole/Systole Detection

Figure 8:
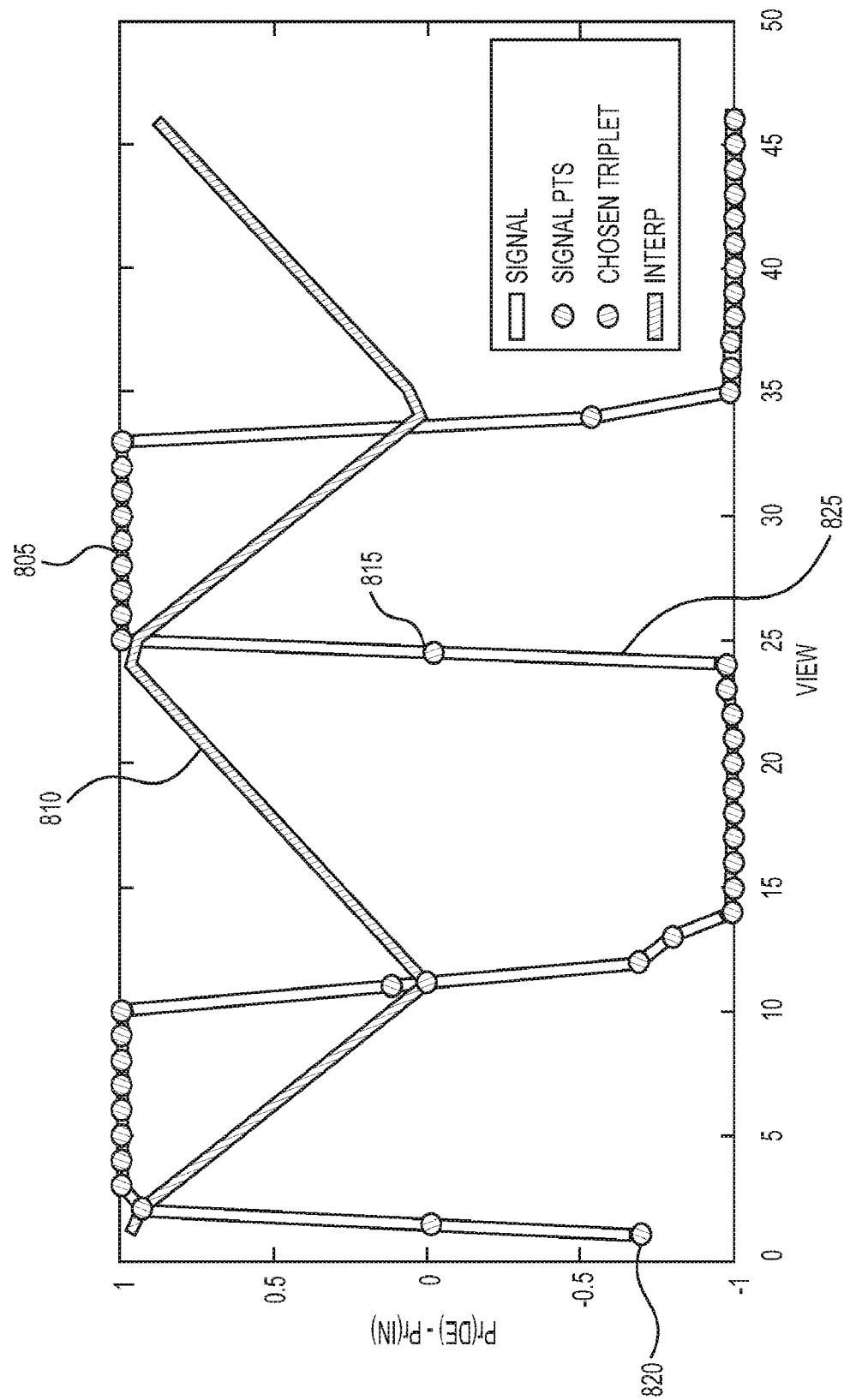
FIG. 8 is an exemplary graph of the detection of the cardiac cycle stage according to an exemplary embodiment of the present disclosure.

The exemplary diastole/systole detection procedure can utilize identifying the cardiac cycle stage of a given input frame $x_i$; where the labels can be $\mathcal{L}=\{DI, SY, IN, DE\}$. The exemplary system, method and computer-accessible medium, according to an exemplary embodiment of the present disclosure, can generate probabilities, for example, only with respect to the non-instantaneous states, IN, DE. FIG. 8 shows an exemplary graph of the detection of the cardiac cycle according to an exemplary embodiment of the present disclosure. For example, line 805 illustrates the difference in probabilities DE minus IN producing values ranging from −1 to 1 for a video clip of test data. Curve 810 was fit with constant deflation and inflation time that best approximates the line 805. The zero crossing of curve 810 can be the detected peak Systole ("SY") and peak Diastole ("DI"); the intermediate stages can be the deflating ("DE") and inflating ("IN") stages. Additionally, as shown in the graph of FIG. 8, points 815 and 820 represent the chosen triplets and the signal points, respectively, while line 825 represents the received signal.

FIGS. 9A-9F show a set of image frames from a cardiac cycle, and in the top-left of each frame the system draws the identified cardiac stage visualized as a dashed circle 905 between two circles indicate peaks systole (e.g., small circle 910) and peak diastole (e.g., large circle 915); the radius of the dashed circle is taken directly from the fitted 710 from FIG. 8.

Exemplary Part Segmentation

Figure 10:
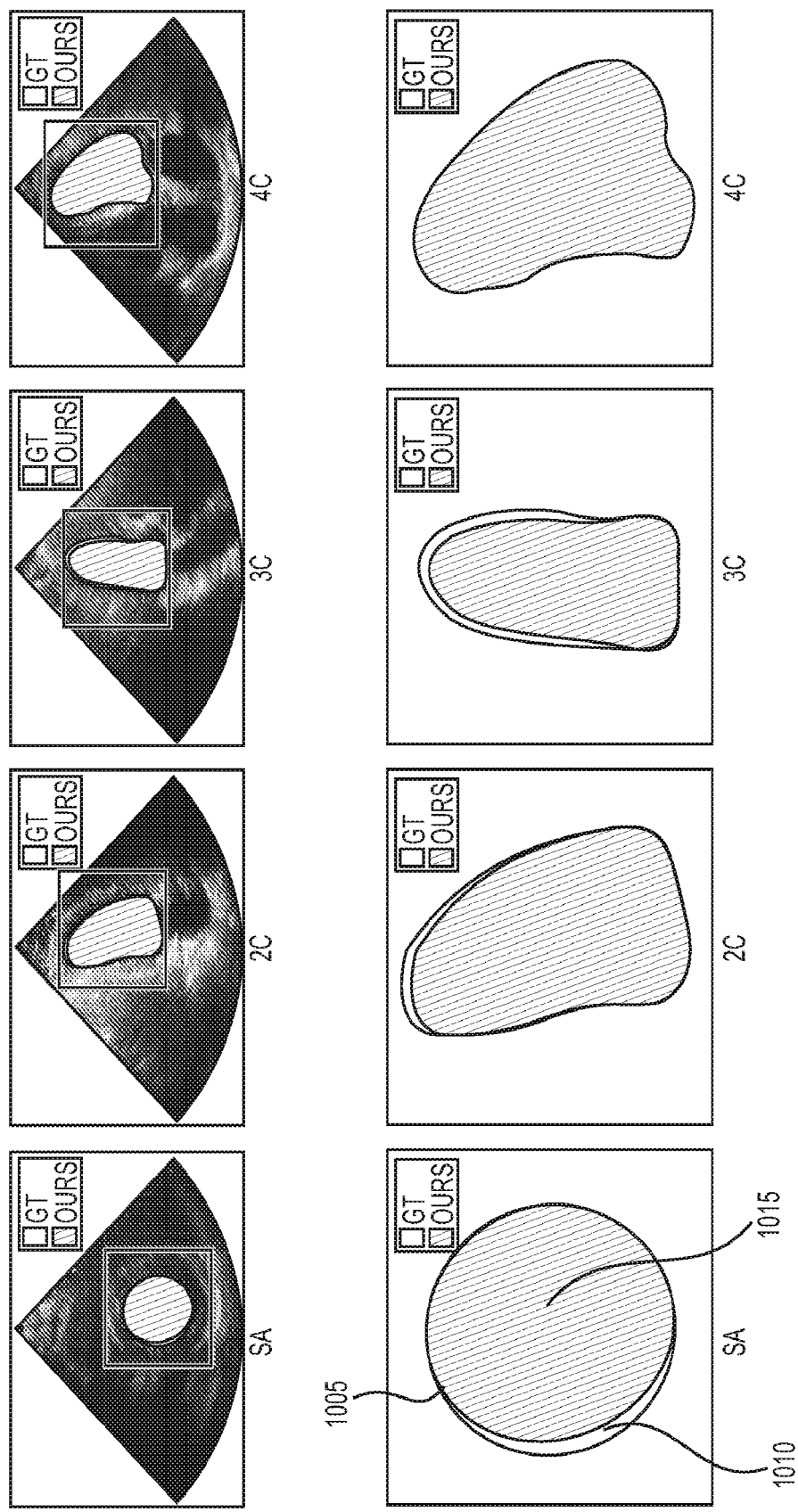
FIG. 10 is a set of images of the segmentation of the left ventricle produced by the exemplary system, method, and computer-accessible medium on four selected views according to an exemplary embodiment of the present disclosure.

The exemplary part segmentation procedure can utilize labeling each pixel in an input image $x_i$ according to the parts labels. For example, only left ventricle ("LV") segmentation can be implemented. FIG. 10 shows a set of images of the segmentation of the LV as produced by the exemplary system, which is illustrated by element 1005. The ground-truth ("GT") user segmentation is illustrated by element 1010, and the overlay of the two is illustrated by element 1015. Note that the segmentation produced by the exemplary system and the user GT can be visually very close. To produce a quantitative analysis to this exemplary procedure, two error measures were computed: (i) Intersection over Union ("IoU") which measures the area of the intersection of the exemplary system's segmentation and GT segmentation divided by the union of both areas (e.g., it can produce the ratio of the common segmented area (e.g., element 1015 shown in FIG. 10)) and the common area plus the different areas (e.g., elements 1005 and 1010 shown in FIG. 10); this ratio can be in the range of 0 to 1, where closer to 1 can be better, and where 1 means the exemplary segmentation and GT can be identical at the pixel level, and (ii) Relative Area Difference ("RAD") measures the difference in area of the segmentation produced by the exemplary system and the GT divided by the GT segmentation area.

Figure 12:
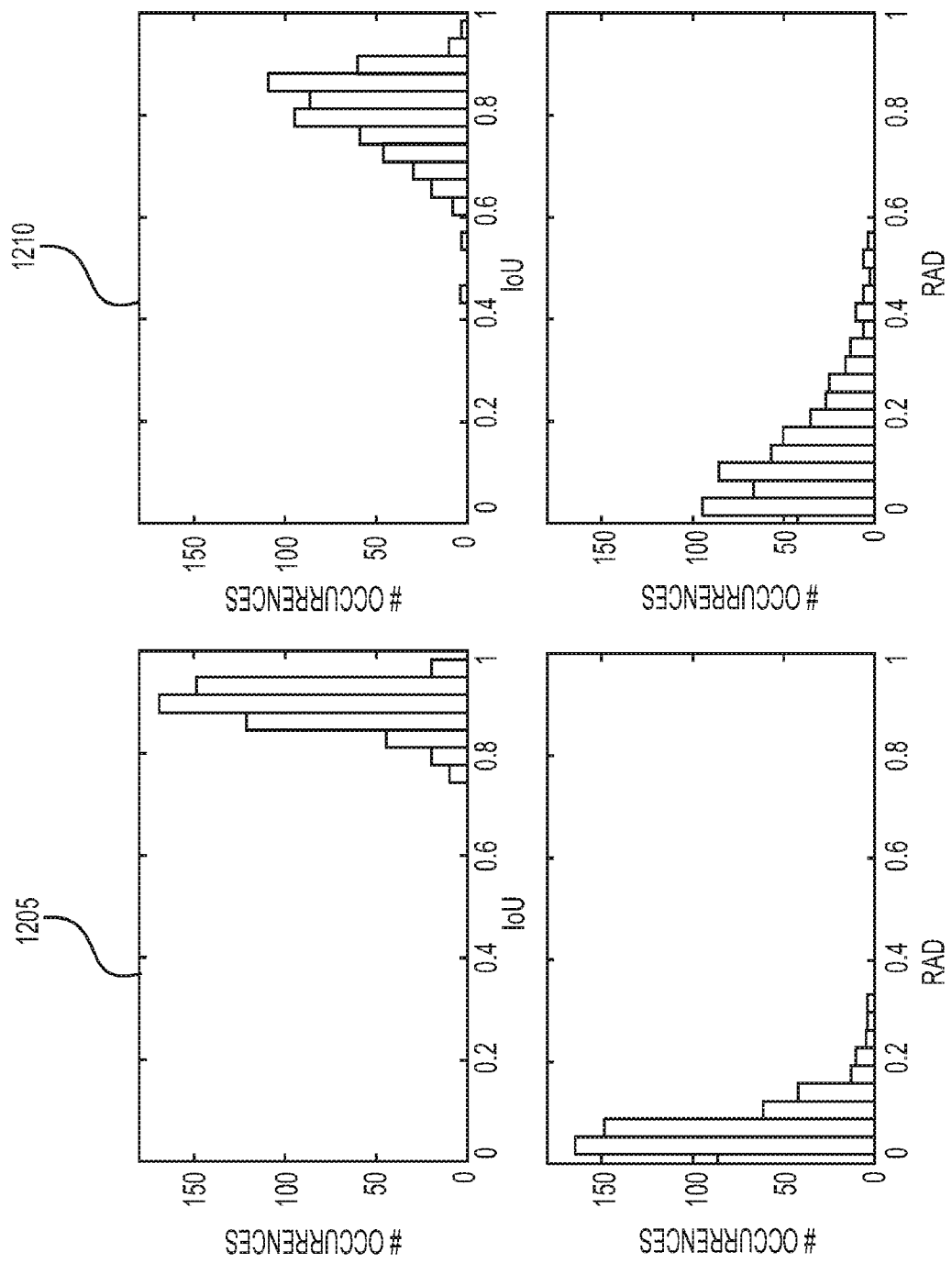
FIG. 12 is a set of exemplary charts of the intersection over union and relative area difference comparing the left ventricle segmentation produced by the exemplary system, method, and computer-accessible medium vs. the ground truth and a user vs. the ground truth according to an exemplary embodiment of the present disclosure.

To produce a baseline for the results, the exemplary user was asked to repeat the LV annotation of the test set after waiting a period of several weeks, and to measure these new segmentations versus the original GT segmentations. FIG. 12 shows four histograms for these two error measures, where, for each error measure, one set of histograms is shown for the exemplary method compared to GT (e.g., set of histograms 1210) and one set of histograms for the user compared to the GT (e.g., set of histograms 1205). The results indicate the exemplary system produces segmentations slightly less consistent with the GT than the user, however comparable; these results can be remarkable when taking into account that the same user marked the two LV segmentations; larger variability in the user vs. GT experiment can be expected when repeating this experiment with a different user.

Exemplary Valve Localization

Figure 13:
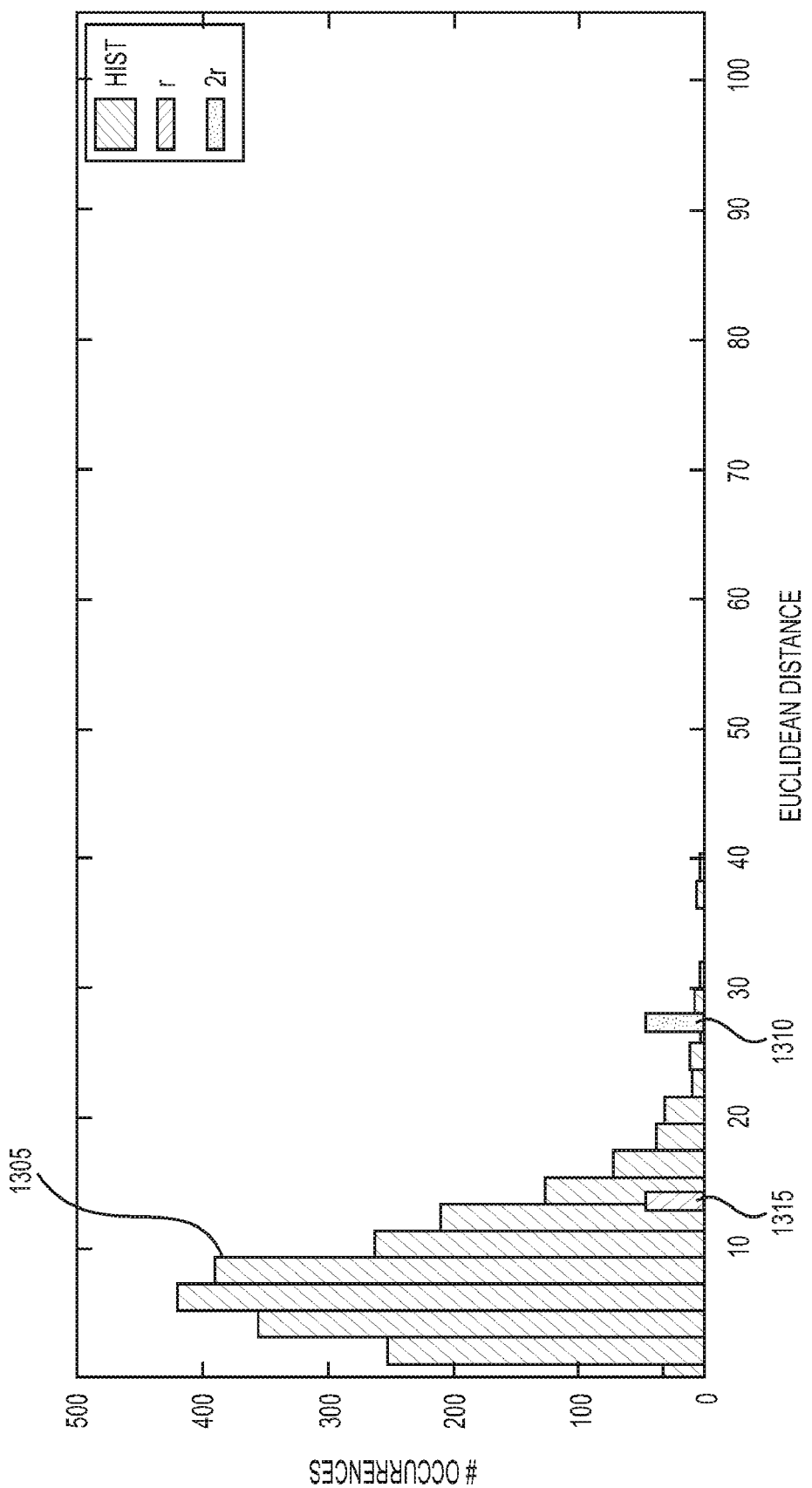
FIG. 13 is an exemplary histogram diagram of the distances between the exemplary system, method, and computer-accessible medium valve localization prediction and ground truth according to an exemplary embodiment of the present disclosure.

This exemplary procedure can utilize placing a point at a certain location for flow calculation during Doppler analysis. FIGS. 11A-11D show exemplary images of the valve localization (e.g., elements 1105) produced by the exemplary system, method and computer-accessible medium, for two views (e.g., FIGS. 11A and 11C) and magnified views (e.g., FIGS. 11B and 11D, respectively). Elements 1110 shown in FIGS. 11A-11D show a disk centered at the user marked valve localization for GT, where the radius can be computed to represent uncertainty in the user localization. The uncertainty can be computed based on data where the user marked valve localization repeatedly 10 times per-frame, and the maximal deviation can be computed from the average prediction; this value can be called an uncertainty radius, and can be labeled by r. FIG. 13 shows an exemplary histogram 1305 of distances between the predicted valve localization of the exemplary system and the ground-truth localization by the user. Markers 1310 and 1315 indicate the uncertainty radius r and two times the uncertainty radius 2r, respectively.

Exemplary Versatility

Figure 14:
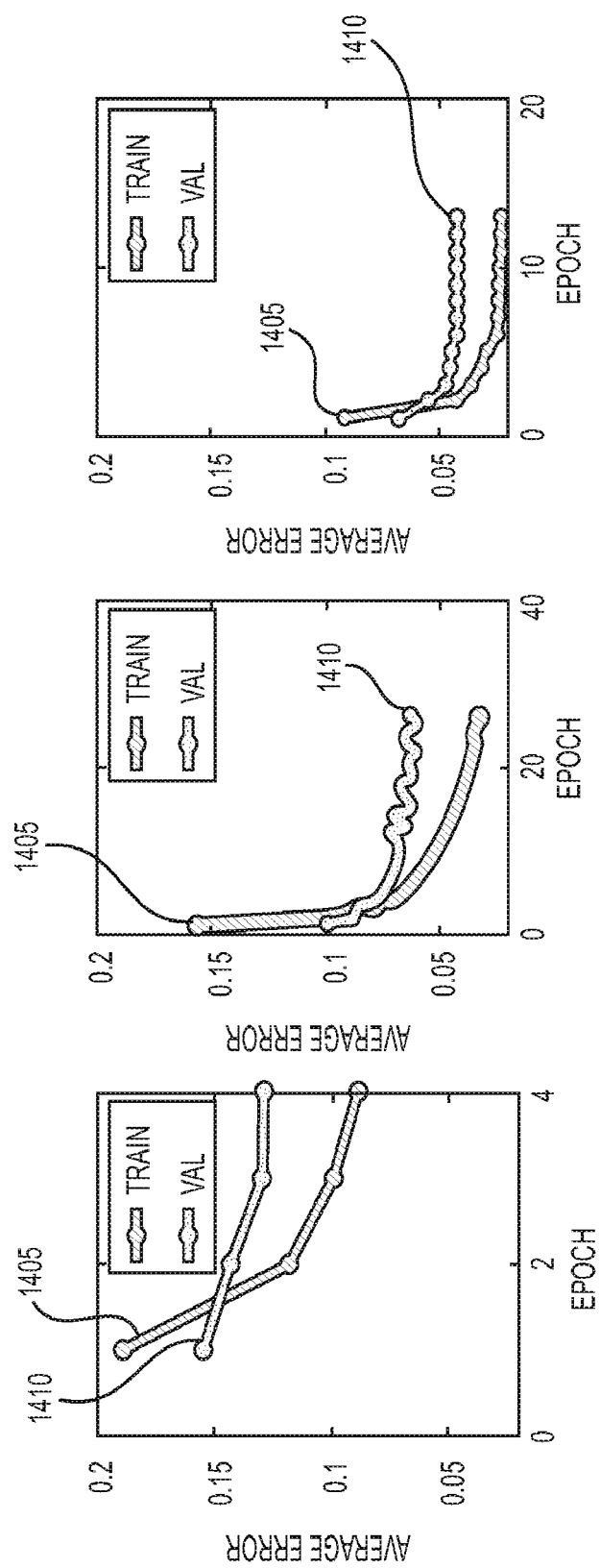
FIG. 14A is an exemplary graph of a learning graph for the Diastole/Systole classification test initialized with imagenet-type network for the Core Neural Network according to an exemplary embodiment of the present disclosure.
FIG. 14B is an exemplary graph of a learning graph for the Diastole/Systole classification test initialized with the Core Neural Network after view detection training according to an exemplary embodiment of the present disclosure.
FIG. 14C is an exemplary graph of a learning graph for the Diastole/Systole classification test initialized with the Core Neural Network after being trained on a part segmentation procedure according to an exemplary embodiment of the present disclosure.

The exemplary Core NN was tested to determine how it can adapt to new procedures after different levels of training and using a "warm start" initialization. FIGS. 14A-14C are exemplary learning graphs for the exemplary Diastole/Systole classification test. For example, these learning graphs depict the train (e.g., element 1405) and validation (e.g., element 1410) error during training of the Diastole/systole procedure when its Core NN can be initialized in three different ways: (i) with the Core NN taken from imagenet-type NN trained on natural images (see, e.g., FIG. 14A); (ii) with the Core NN after being trained on the view detection procedure (see, e.g., FIG. 14B) and (iii) with Core NN after being trained on the part segmentation procedure (see, e.g., FIG. 14C). Initializing the system with Core NN that already learned some ultrasound analysis procedure (e.g., view detection) produced much more accurate results in shorter training time (e.g., compare FIGS. 14A and 14B). After learning the segmentation and repeating the DS training, the results even further improve (e.g., compare FIGS. 14B to 14C). This exemplary experiment supports that: (i) the different procedures corroborate and facilitate higher accuracy and better performance and (ii) initializing a procedure with the Core NN from a different ultrasound procedure can facilitate learning, and can achieve higher performance.

The exemplary system, method and computer-accessible medium, according to an exemplary embodiment of the present disclosure, can be used as an add-on to any clinical commercial imaging device, (e.g., ultrasound). The exemplary system, method and computer-accessible medium can be used for both the Echocardiography (e.g., Ultrasound of the Heart) in the Cardiology Department and the Emergency Department ("ED").

Exemplary Cardiac Function And Measurements

Figure 15:
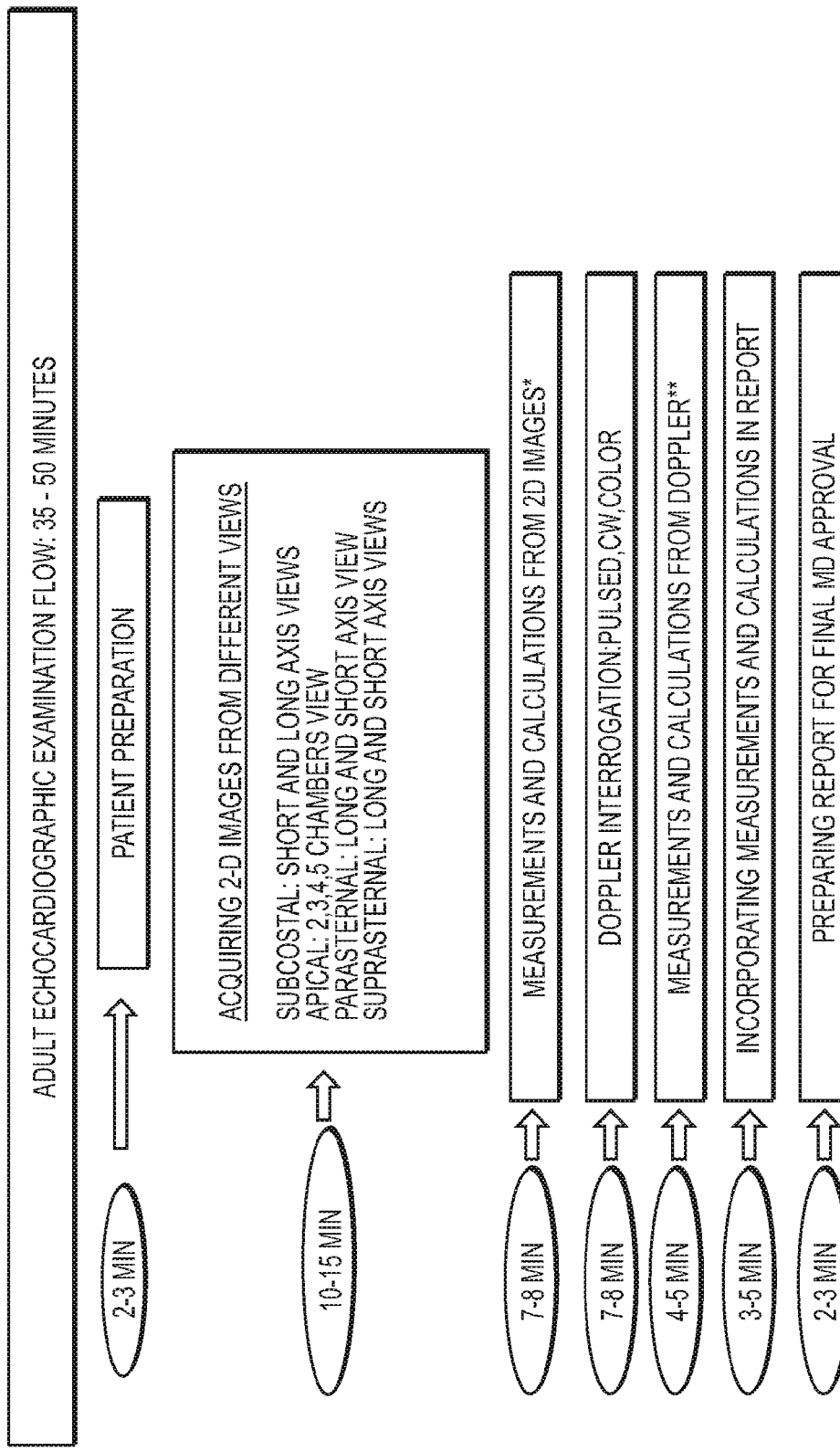
FIG. 15 is an exemplary flow diagram illustrating an adult echocardiographic examination performed using an exemplary procedure according to an exemplary embodiment of the present disclosure.

Multiple technicians were observed while performing a routine and complete Echocardiographic examination. The total duration of the examination and the distribution of time for each of the three tasks were recorded. (See, e.g., diagram of FIG. 15). About 50% of the total time was dedicated to image acquisition, about 30% to about 35% was used for analysis, including tracing online measurement and calculation and about 10% to about 15% was used to generate a report. (See e.g., diagram shown in FIG. 15).

The exemplary system, method and computer-accessible medium, according to an exemplary embodiment of the present disclosure, can be used to accurately identify the left ventricle (e.g., out of the 4 chambers), and automatically apply and provide a complete cardiac function analysis that can be incorporated directly into the final study report. Currently, the technician has to identify two or three points, or trace the left ventricle in different views (e.g., out of the six views acquired), and then activate the calculation packages available on an exemplary machine. The exemplary system, method and computer-accessible medium, according to an exemplary embodiment of the present disclosure, can automatically detect the different viewing windows and segments, and can identify the various parts of the heart, such as the left ventricle.

The exemplary system, method and computer-accessible medium, according to an exemplary embodiment of the present disclosure, can use segmentation, peak systolic and/or peak diastolic frames, which can now be determined automatically. In the past, this has been performed manually by the technician by carefully scanning frame by frame, and identifying the peak systolic and peak diastolic frame. The exemplary system, method and computer-accessible medium, according to an exemplary embodiment of the present disclosure, can utilize a neural core to determine these two events during the cardiac cycles, and can then perform an assessment of the left ventricular function. Thus, the manual labor can be eliminated completely, and all other measurements, including dimension of the left ventricle in systole and diastole, Right ventricular assessment, LA size, measurement of the aortic valve annulus, the aortic sinuses, the ascending aorta, the pulmonary valve, the mitral valve annulus and the tricuspid valve annulus, can be automatically measured.

An important part of the cardiac examination by a skilled echocardiographer can be to perform a thorough Doppler examination. In the past, the technician identified the ideal location and angle in which the sample volume of the Doppler can be located to receive the best signal-to-noise ratio. This can also be a manually laborious task that requires expertise in order to assess all cardiac valves. Such task is time consuming. The exemplary system, method and computer-accessible medium, according to an exemplary embodiment of the present disclosure, can be used to identify the exact area where Doppler samples can be located. After the appropriate image can be achieved, a Doppler sample location can be identified, and the exemplary system, method and computer-accessible medium, according to an exemplary embodiment of the present disclosure, can automatically activate the Doppler modality, thus achieving appropriate Doppler tracing across the cardiac valves. When Doppler tracings is achieved and displayed, calculation packages can be applied, and the mitral and tricuspid valve inflow, as well as the aorta and pulmonary outflow tract Doppler tracing, can be calculated automatically.

About 10%-15% of the total duration of the examination can be dedicated to incorporate all measurements in the final report before it can be sent to the specialist, for example, the cardiologist who can finalize the report and send it to emergency medical records. This can be a significantly manual process that can be avoided by automatically measuring, using the exemplary system, method and computer-accessible medium, all the different variables needed to assess cardiac function as well as valve abnormalities. (See e.g., diagram shown in FIG. 15).

It is estimated that the exemplary system, method and computer-accessible medium, can save up to 40% of the time as compared to a manual exam (e.g., the type of examinations currently being performed). Additionally, the exemplary system, method and computer-accessible medium, according to an exemplary embodiment of the present disclosure, can improve efficiency as well as quality as compared to currently-performed manual exams.

The exemplary system, method, and computer-accessible medium, according to an exemplary embodiment of the present disclosure, can, after the appropriate image is acquired by the technician/physician/nurses, automatically display cardiac function as normal, mild, moderate or severe left ventricular dysfunction. If needed, the exact number of Left Ventricular Ejection Fraction can also be displayed.

Exemplary Pericardial Effusion

Pericardial effusion represents one of the most dangerous cardiac abnormalities that can lead to death if not diagnosed in a timely fashion. The exemplary system, method and computer-accessible medium, according to an exemplary embodiment of the present disclosure, can be used to automatically detect the existence of pericardial effusion by ultrasound examination. For example, the exemplary system, method and computer-accessible medium, according to an exemplary embodiment of the present disclosure, can (e.g., detect immediately) any pericardial effusion, and alert the operator by the existence or nonexistence of pericardial effusion. If needed, the severity of the accumulated pericardial effusion can be displayed.

Exemplary Segmental Abnormality

Cardiac segmental abnormalities can be used as a screening tool for the diagnosis of ischemia of the cardiac muscle. This can be a very subjective task, and can be operator-dependent even in the hands of an expert cardiologist. The exemplary system, method and computer-accessible medium, according to an exemplary embodiment of the present disclosure, can automatically notify the user that there may be segmental abnormalities, for example, Hypokynesis, diskynesia or paradoxical motion of any part of the left ventricular wall and septum. Currently, the heart is divided into 17 segments and the exemplary system, method and computer-accessible medium, according to an exemplary embodiment of the present disclosure, can detect very subtle wall motion abnormalities across all segments.

Exemplary RV-To-LV Ratio

The exemplary system, method and computer-accessible medium can use the exemplary neural core to identify and separate the left and the right ventricles. The exemplary neural core can assess the relative and absolute areas and volumes of these ventricles, and can quickly calculate the ratio between them (e.g., in a fraction of a second). This can be beneficial in order to raise the suspicion level of a critical condition called a pulmonary embolism. In this condition there can be a major strain on the right ventricle, and as a result, the ventricle tends to enlarge, and the ratio between right ventricle and left ventricular area can be dramatically altered. This can be used as an exemplary screening tool to notify the clinician that there can be a possible pulmonary embolism based on the RV-to-LV ratio. (See e.g., diagram shown in FIG. 16).

Figure 16:
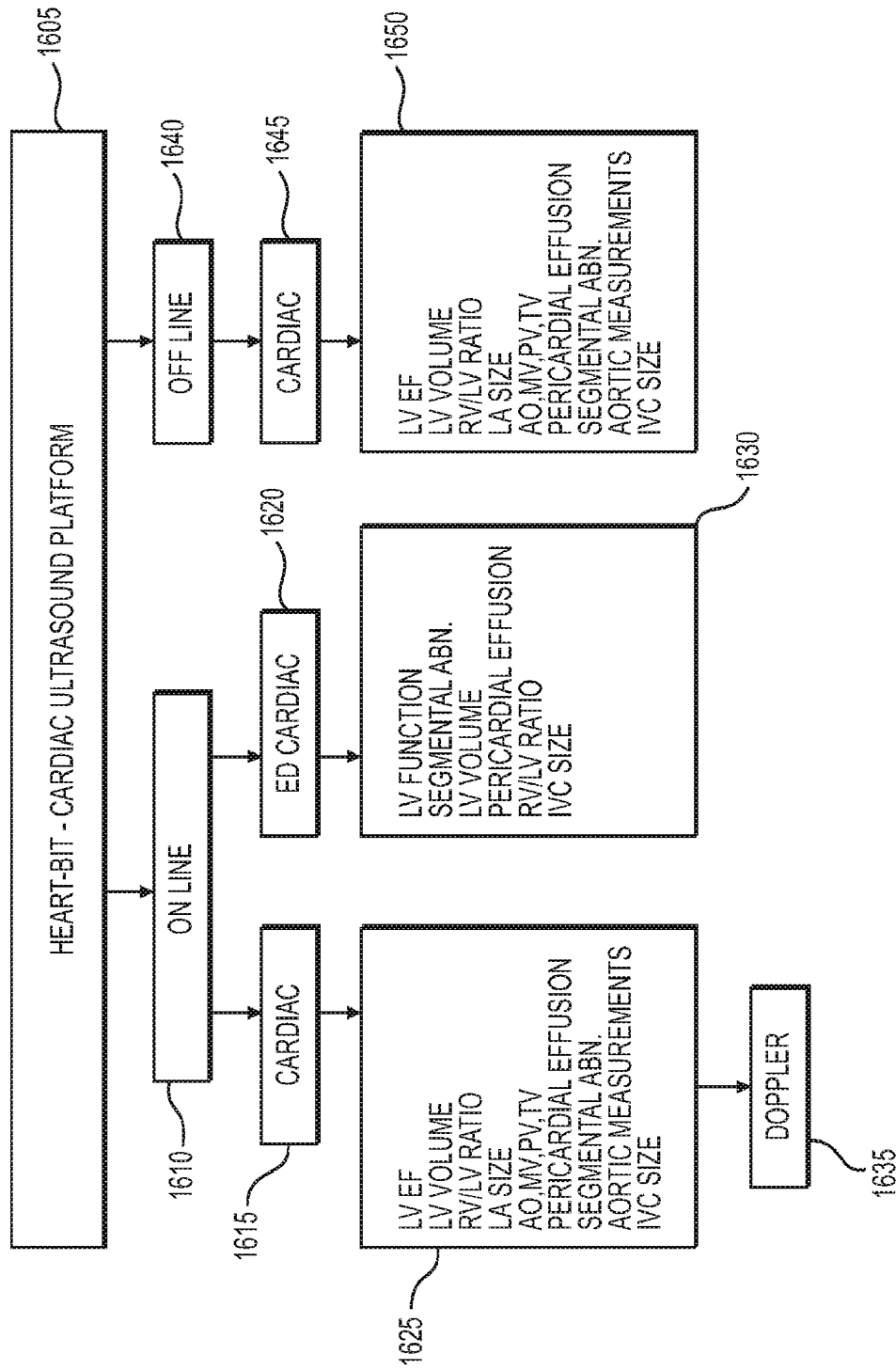
FIG. 16 is an exemplary diagram of an exemplary configuration of the exemplary system, method and computer-accessible medium, for use in cardiac ultrasound according to an exemplary embodiment of the present disclosure.

For example, as illustrated in an exemplary diagram of FIG. 16, a cardiac ultrasound platform 1605 can be used in either on online mode 1610 or an offline mode 1640. In the online mode 1610, the cardiac ultrasound platform can be used in a cardiac setting 1615 or an ED cardiac setting 1620. Various functions 1625 can be performed in the cardiac setting 1625, which can be based on a Doppler analysis 1635 (e.g., (i) LV EF, (ii) LV Volume, (iii) RV/LV Ratio, (iv) AO, MV, PV, TV, (v) Pericardial Effusion, (vi) Segmental Abn., (vii) Aortic Measurements, and (viii) IVC size). Further functions 1630 can be performed in the ED cardiac setting 1620 (e.g., (i) LV Function, (ii) Segmental Abn., (iii) LV Volume, (iv) Pericardial Effusion, (v) RV/LV Ratio, and (vi) IVC size). In offline mode 1640, in a cardiac setting 1645, various offline functions 1650 can be performed (e.g., (i) LV EF, (ii) LV Volume, (iii) RV/LV Ratio, (iv) AO, MV, PV, TV, (v) Pericardial Effusion, (vi) Segmental Abn., (vii) Aortic Measurements, and (viii) IVC size).

Exemplary Ejection Fraction

Figure 19A:
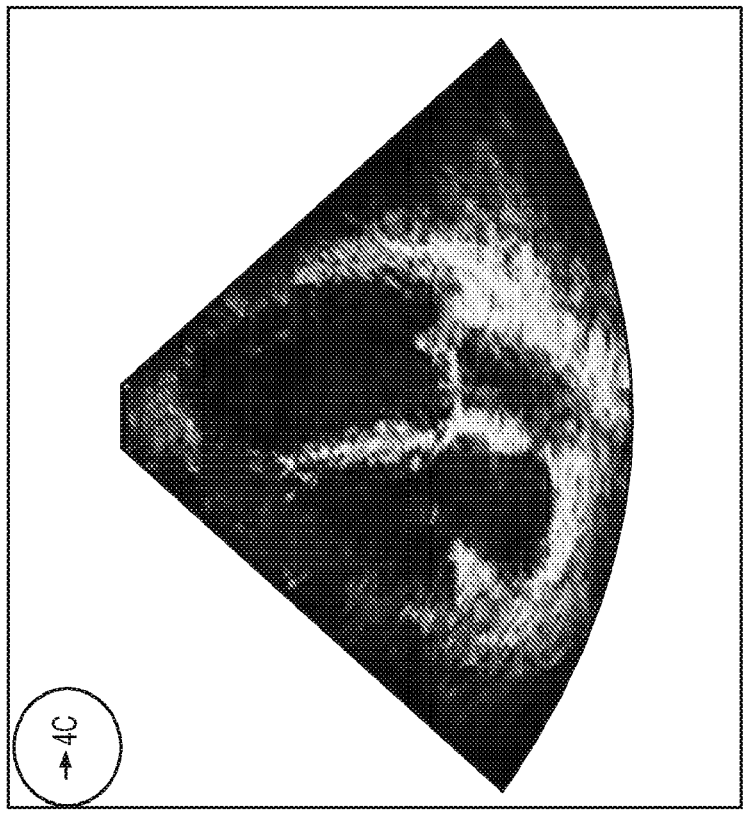
FIG. 19A is an exemplary image generated based on a user interface left drive mode according to an exemplary embodiment of the present disclosure.
Figure 19B:
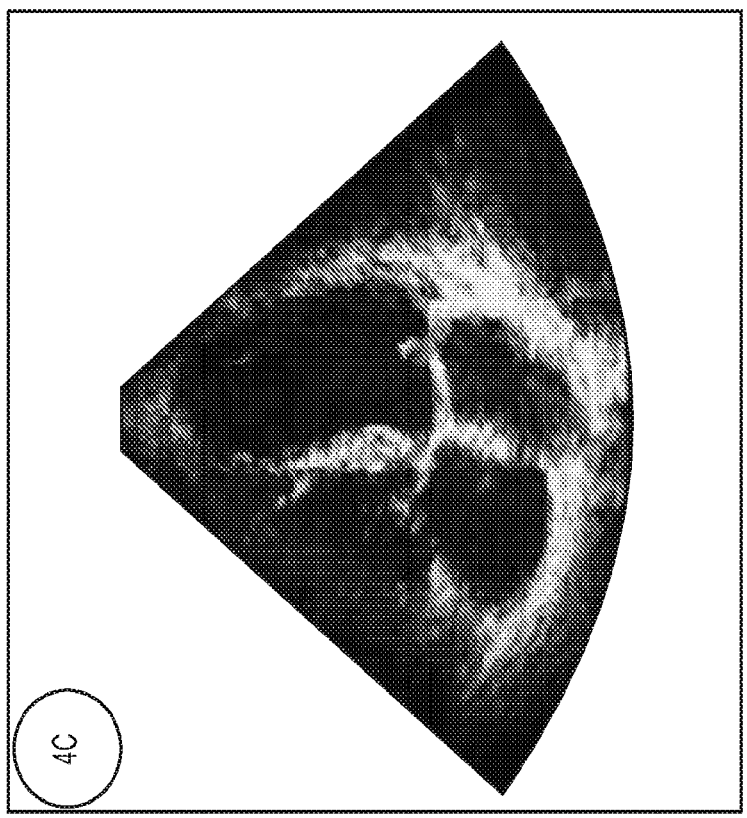
FIG. 19B is an exemplary image generated based on a user interface right halt mode according to an exemplary embodiment of the present disclosure.
Figure 20A:
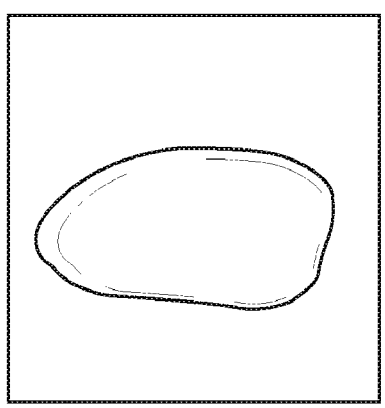
FIGS. 20A-20G are exemplary images of a 3D reconstruction of a full cardiac cycle according to an exemplary embodiment of the present disclosure.
Figure 20B:
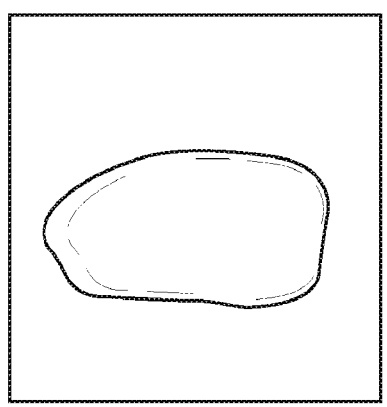
Figure 20C:
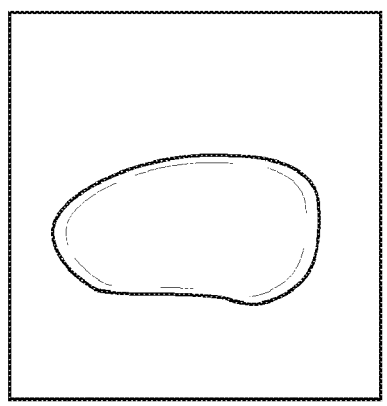
Figure 20D:
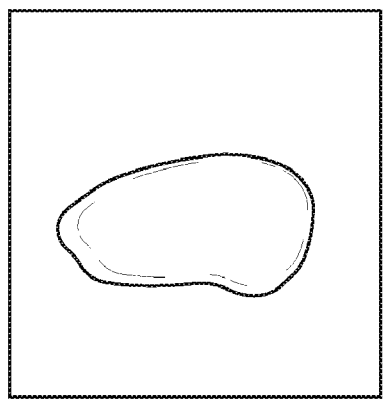
Figure 20E:
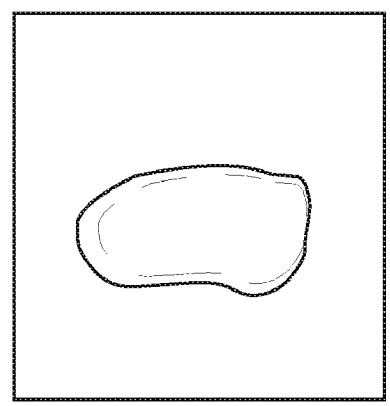
Figure 20F:
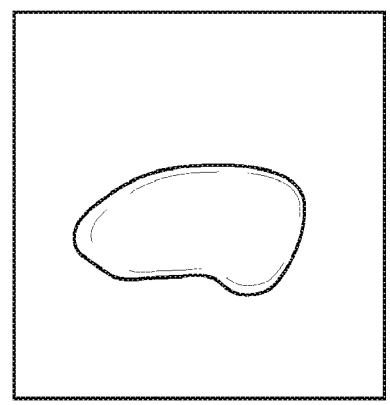
Figure 20G:
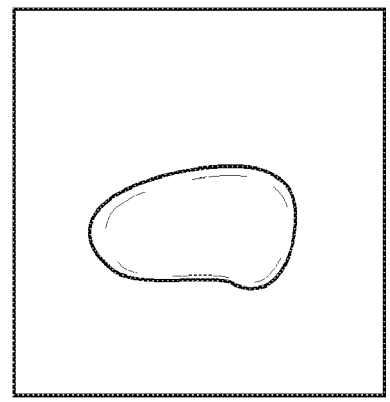

The exemplary system, method and computer-accessible medium, according to an exemplary embodiment of the present disclosure, can be used to compute or otherwise determine the EF from the raw UT input. The user can be provided with, for example, the indication of one of two possibilities: (i) a drive and (ii) a halt. In drive (see, e.g., FIG. 19A) the user can be instructed to navigate the UT transducer to produce the desired view (e.g., 4C, 2C, SA, etc.). When a halt sign is shown (see, e.g., FIG. 19B) the user can be requested to hold still while the exemplary system, method and computer-accessible medium, according to an exemplary embodiment of the present disclosure, gathers information. After traversing the exemplary views, the exemplary system, method and computer-accessible medium, can automatically produce the EF prediction along with the 3D reconstruction of the LV.

The exemplary determination of the EF can include the following exemplary procedures:

(i) Each input triple Xi can be passed through the exemplary network to produce a View detection and LV segmentation.

(ii) A time versus area curve can be computed for each view.

(iii) Persistence diagrams can be used to find stable maximum and minimum points of these curves.

(iv) From each view, all maximum and minimum cross sections can be extracted.

(v) The 3D volumes of the systole and diastole of the LV can be reconstructed by considering all combinations of minimal cross sections and maximal cross sections.

(vi) For each collection of cross sections (e.g., all of the same type: either minimal or maximal), the cross section can be aligned in 3D space. (See e.g., FIG. 21A which illustrates one collection of minimum cross sections in image 2105 and one collection of maximum cross sections in image 2110).

(vii) A 3D mesh M=(V, E, F) can be fitted, with vertices V, edges E, and faces F, to the cross sections by constraining the boundary of the cross sections to be on the mesh surface while minimizing the Willmore energy, $\int_M H^2 dA$, of the surface, where H can be the mean curvature and dA can be the area element on the surface. The Willmore energy can be used to minimize distortion, and can be optimal for round spheres. The exemplary optimization can be performed by a gradient descent together with a line search strategy. FIG. 21B shows the reconstruction generated using the cross sections in FIG. 21A.

(viii) From each pair of systole and diastole reconstruction, a candidate EF can be measured. The final robust estimation of the EF can be generated as the median of the EF histogram. FIG. 22 shows an exemplary histogram (EF Histogram 2202 and EF Prediction 2210) and the extracted value.

The exemplary system, method and computer-accessible medium, according to an exemplary embodiment of the present disclosure, can utilize the above exemplary procedures to produce a 3D reconstruction of the entire cardiac cycle. (See, e.g., FIGS. 20A-20G).

Figures 23A, 23B:
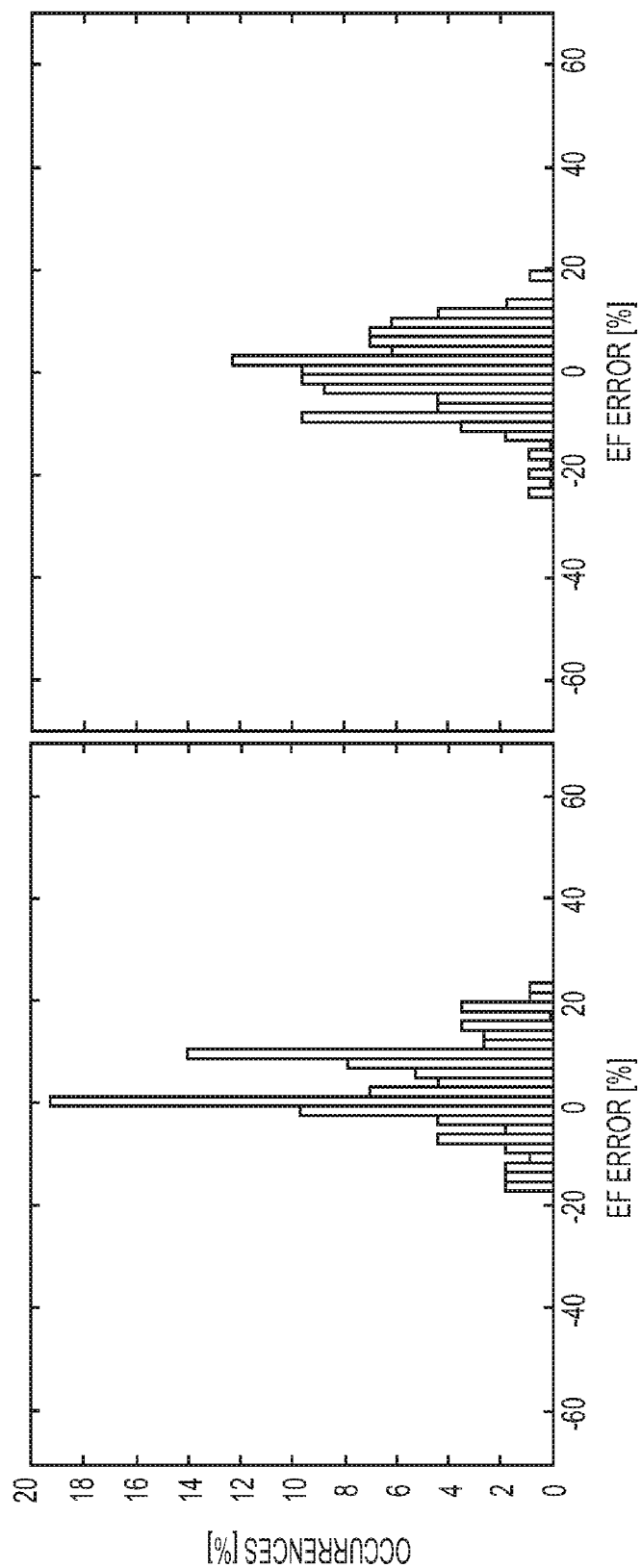
FIG. 23A is an exemplary histogram of EF errors generated based on an exemplary expert analysis of a cardiac cycle according to an exemplary embodiment of the present disclosure.
FIG. 23B is an exemplary histogram of errors generated using the exemplary system, method and computer-accessible medium according to an exemplary embodiment of the present disclosure.

To validate the automatic EF procedure described above, a test of 114 anonymous cases was performed, and compared to 4 expert cardiologists and 2 two expert technicians to assess/compute the EF. The ground truth for each case was defined as the median of these assessments. The exemplary system, method and computer-accessible medium, according to an exemplary embodiment of the present disclosure, was compared to the experts in terms of a mean deviation to ground truth and a standard deviation. As can be seen in Table 1 below, the exemplary system, method and computer-accessible medium produced comparable results to the top experts, and compares favorably to most experts. FIGS. 23A and 23B show the exemplary histogram of the errors of the experts (e.g., see FIG. 23A) and the errors of the exemplary system, method and computer-accessible medium (e.g., see FIG. 23B).

TABLE 1

Comparison of mean and standard deviation of EF estimation errors on 114 subjects based on a comparison of the exemplary system, method and computer-accessible medium to various experts with respect to ground-truth EF.

| Method | Mean EF Error | Std |
|---|---|---|
| Ours | 0.2554862 | 7.388649 |
| Expert1 | −0.2661642 | 8.699921 |
| 3D-GT | 0.5572847 | 4.356815 |
| Expert2 | −0.9854624 | 6.826413 |
| Report-GT | 2.146116 | 5.323971 |
| Expert4 | 3.189976 | 7.996613 |
| Sim-GT | −4.851627 | 5.246874 |
| Bul-GT | 5.107598 | 8.6520291 |
| Expert3 | −8.397743 | 8.327786 |

Exemplary Use Emergency Department

The use of ultrasound in the emergency department is commonplace. The emergency department of a hospital or a medical center can be one of the busiest, stressed and scary places in the healthcare system. The need for a fast and reliable diagnosis can be crucial in order to improve patient outcome. Ultrasound currently has an important role in the following exemplary areas: Pulmonary, cardiac, abdominal scanning and OB-GYN. Additionally, acute scanning of orthopedic abnormalities, including fractures, has been introduced and incorporated into the ultrasound examination in the emergency department. The evolution of handheld devices that facilitate the clinician to scan without searching for equipment in the emergency department facilitates the process for critical decision while also gaining procedural guidance with high-quality ultrasound imaging.

The attraction of immediate bedside sonographic examination in the evaluation of specific emergent complaints can make it an ideal tool for the emergency physician. The increasing pressure to triage, diagnose, and rapidly treat the patient has fueled ultrasound use as the primary screening tool in the emergency department. The major areas currently being used in the ED are abdominal, pelvic, cardiac, and trauma.

Currently, for example, a minimum of 12 months of specific training is needed in order to train an emergency department physician to become an expert in ultrasound. There is an official ultrasound fellowship for emergency department physicians that takes a full 12 months of training. Not every emergency department in the country is currently staffed by an expert ultrasonographer. Thus, the exemplary system, method and computer-accessible medium, can assist the physician in the emergency room quickly identify abnormalities in different body systems.

Exemplary Cardiac Ultrasound in the Emergency Department

Emergent cardiac ultrasound can be used to assess for pericardial effusion and tamponade, cardiac activity, infarction, a global assessment of contractility, and the detection of central venous volume status, as well as a suspected pulmonary embolism. Ultrasound also has been incorporated into resuscitation of the critically ill and the at-risk patients. In the assessment of a patient with undifferentiated hypotension, emergent cardiac ultrasound can also be expanded for the use in heart failure and dyspnea. The exemplary system, method and computer-accessible medium, according to an exemplary embodiment of the present disclosure, can perform the following exemplary functions:

Exemplary Abnormal Segmental Movement.

The exemplary system, method and computer-accessible medium, according to an exemplary embodiment of the present disclosure, can also alert the operator if there can be abnormal motion including akinesia, hypokinesia, dyskinesia and paradoxical movement of any part of the ventricular wall and septum, indicating potential ventricular ischemia or infarction. Left Ventricular Volume can be displayed in situations of Hypovolumia. (See e.g., diagram shown in FIG. 16).

The exemplary system, method and computer-accessible medium, according to an exemplary embodiment of the present disclosure, can be used in an emergency department for the following exemplary examinations:

1) Focused assessment with sonography in trauma or fast (examination).
2) Pregnancy.
3) Abdominal aortic aneurysm.
4) Hepatobiliary system.
5) Urinary tract.
6) Deep vein thrombosis.
7) Soft tissue musculoskeletal.
8) Thoracic airway.
9) Ocular.
10) Bowel.

The exemplary uses of ultrasound in the emergency department have the potential to use deep learning for a faster and more acute diagnosis.

Emergency physicians' use of ultrasound can provide timely and cost-effective means to accurately diagnose emergency conditions during illness and injury in order to provide a higher-quality, lower-cost, care. ED ultrasound use can often reduce the need for more expensive studies such as CT or MRIs and can reduce unnecessary admissions for more comprehensive diagnostic workup. Additionally, the moving of the patient from one lab to the other requires manpower and complex queue scheduling and monitoring. Thus, the exemplary system, method and computer-accessible medium, according to an exemplary embodiment of the present disclosure, can provide a new way of using ultrasound in the emergency department. (See e.g., diagram shown in FIG. 17).

Figure 17:
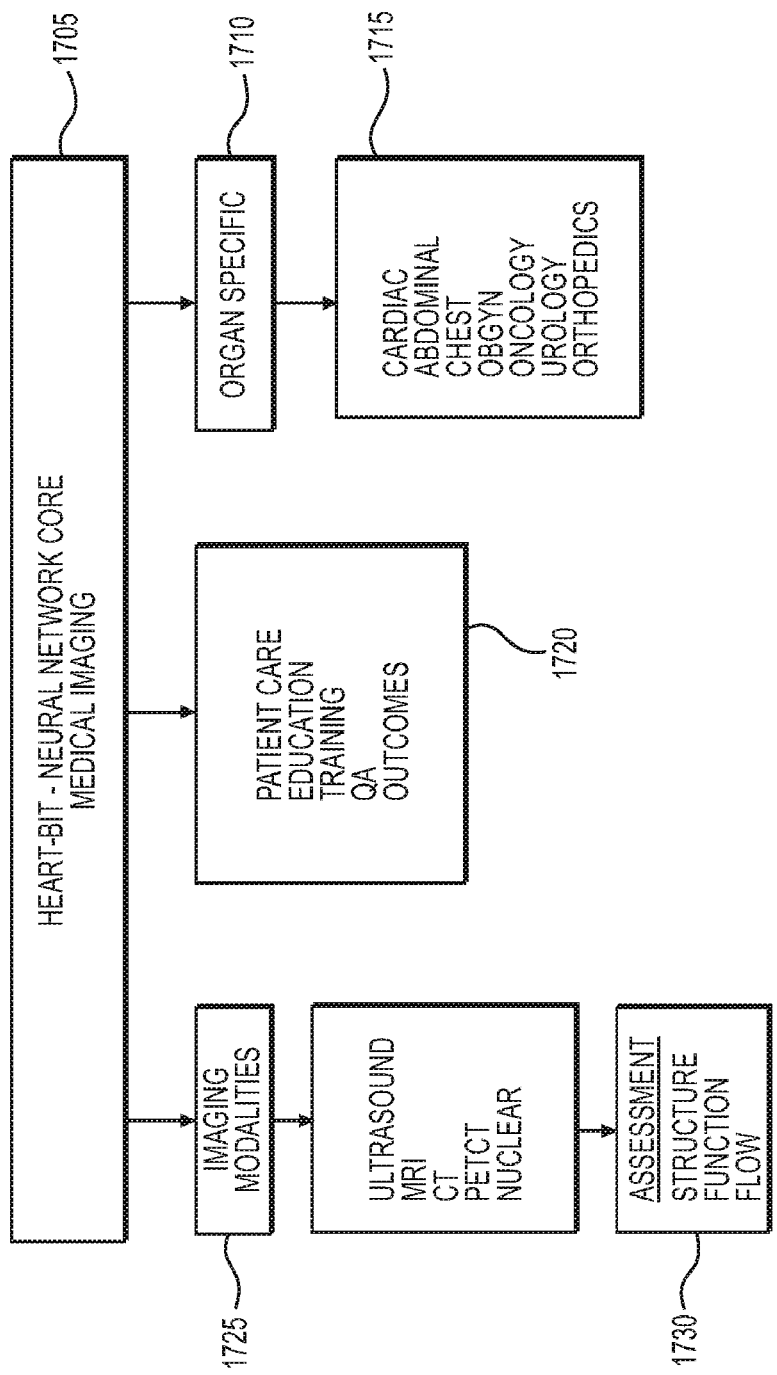
FIG. 17 is an exemplary diagram illustrating the neural network core of the exemplary system, method and computer-accessible medium according to an exemplary embodiment of the present disclosure.

For example, as shown in an exemplary diagram of FIG. 17, neural network core medical imaging 1705 can be performed, e.g., using the exemplary system, method and/or computer-accessible medium according to exemplary embodiments of the present disclosure. This can be organ specific 1715, based on various organs, organ types, or medical specialties 1715 (e.g., (i) cardiac, (ii) abdominal, (iii) chest, (iv) OBGYN, (v) oncology, (vi) urology, and (vii) orthopedics. Neural network core medical imaging 1705 can be used in various settings 1720 (e.g., (i) patient care, (ii) education, (iii) training, (iv) quality assurance ("QA"), and (v) outcomes. Various imaging modalities 1725 can be used (e.g., (i) ultrasound, (ii) magnetic resonance imaging ("MRI"), (iii) computed tomography ("CT"), (iv) positron emission tomography CT ("PETCT"), and (v) nuclear).

Figure 18:
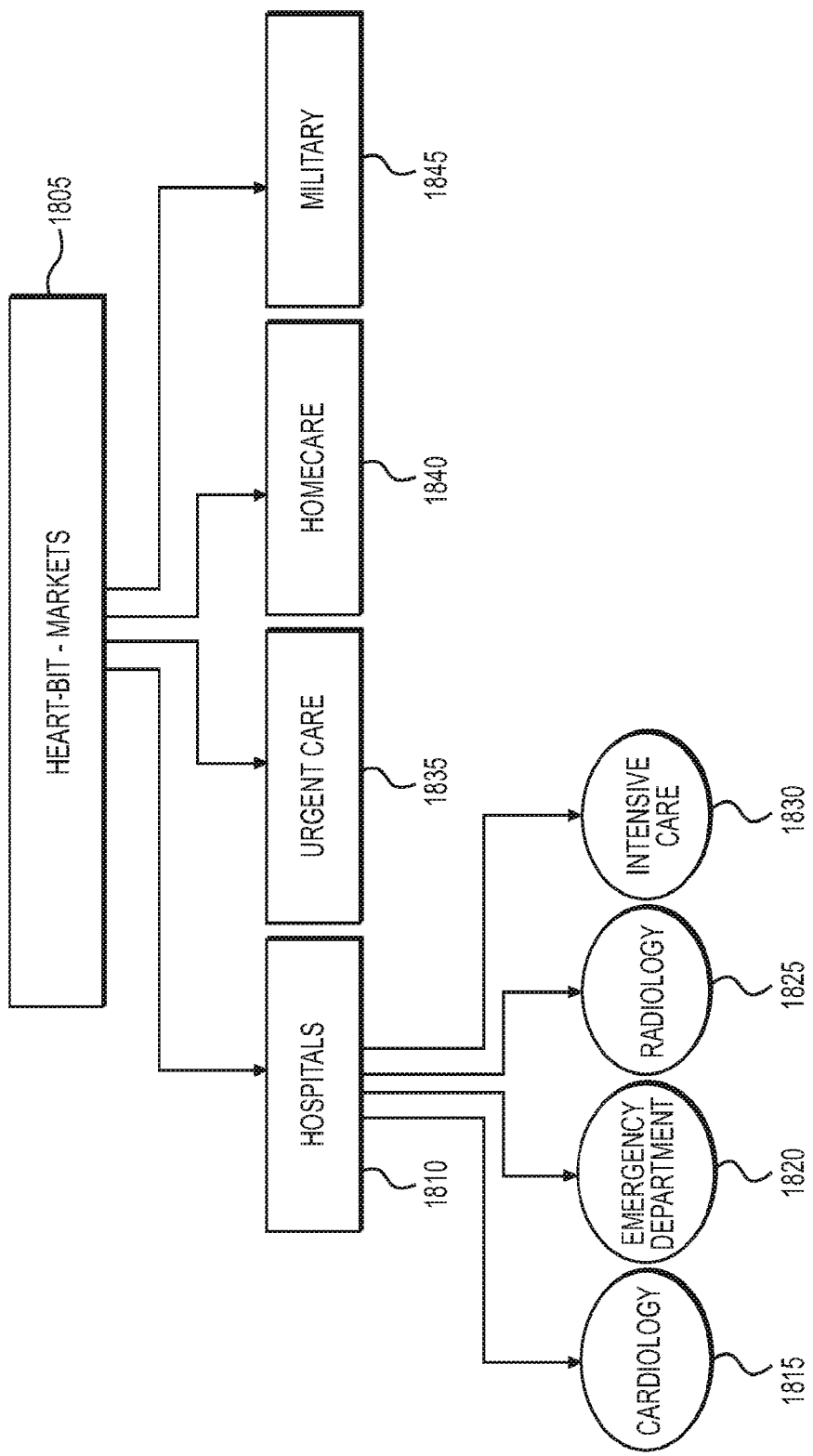
FIG. 18 is an exemplary diagram illustrating potential markets in which the exemplary system, method and computer-accessible medium, can be used according to an exemplary embodiment of the present disclosure.

An exemplary assessment of the examination can result in improving point of care. Using established analytic tools can facilitate much faster and reliable diagnosis. There can be no need for major requirements for special training. The exemplary system, method and computer-accessible medium, according to an exemplary embodiment of the present disclosure, can be used in other fields including military arena, telemedicine applications, urgent care facilities and in-home healthcare. (See e.g., diagram shown in FIG. 18). Exemplary markets 1805 for the use of the exemplary system, method, and computer-accessible medium, can include hospitals 1810 (e.g., in (i) cardiology 1815, (ii) ED 1820, (iii) radiology 1825, and (iv) intensive care 1830), urgent care 1835, homecare 1840, and the military 1845.

Figure 24:
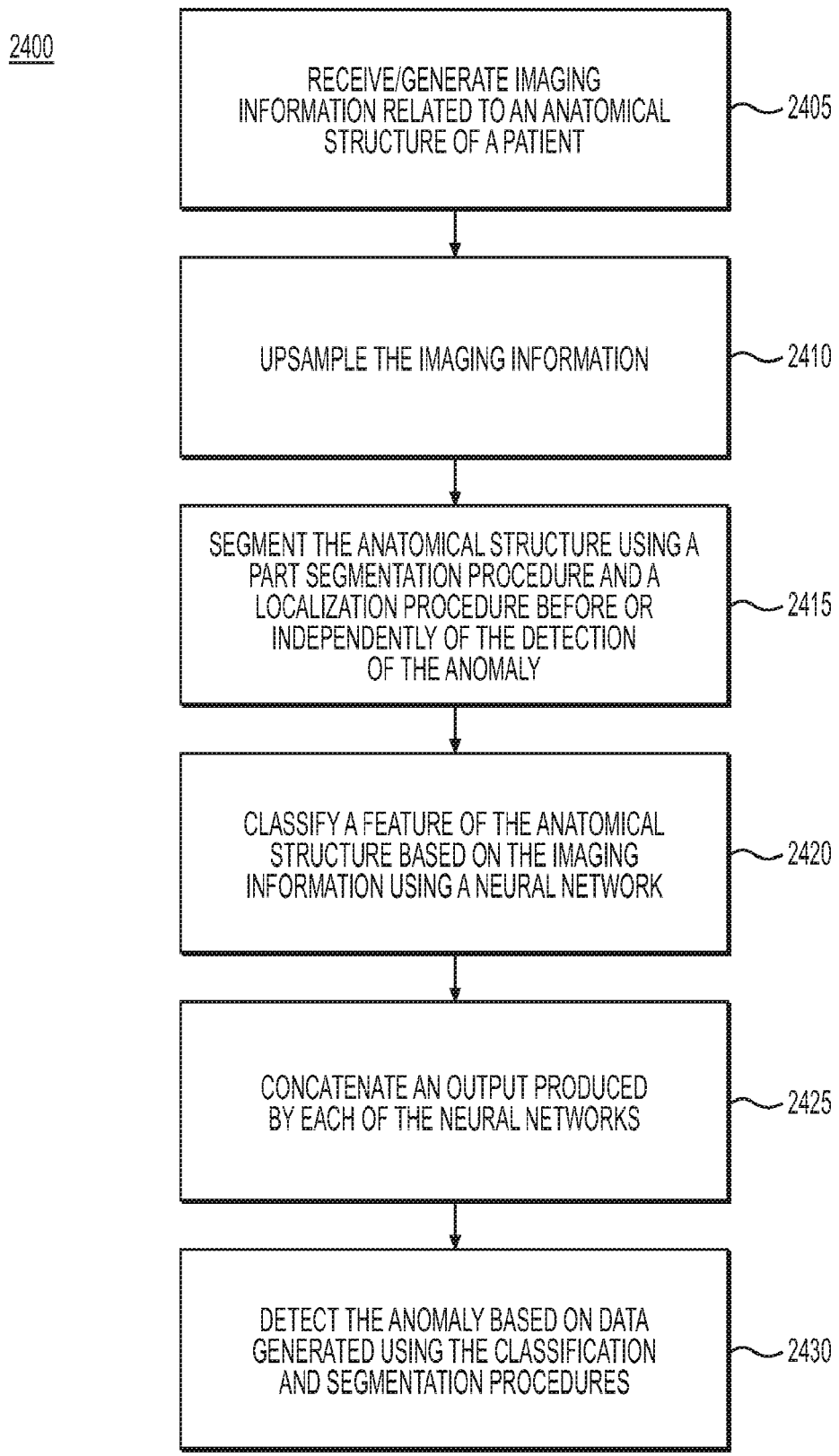
FIG. 24 is an exemplary flow diagram of an exemplary method for detecting an anomaly in an anatomical structure of a patient according to an exemplary embodiment of the present disclosure.

FIG. 24 illustrates an exemplary flow diagram of an exemplary method 2400 for detecting an anomaly in an anatomical structure of a patient according to an exemplary embodiment of the present disclosure. For exemplary, at procedure 2405, imaging information related to an anatomical structure of a patient can be generated or received. At procedure 2410, the imaging information can be optionally upsampled. At procedure 2415 the anatomical structure can be segmented using a part segmentation procedure and a localization procedure before or independently of the detection of the anomaly. At procedure 2420, a feature of the anatomical structure can be classified based on the imaging information using a neural network. At procedure 2425, an output produced by each of the neural networks can be concatenated. At procedure 2430, the anomaly can be detected based on data generated using the classification and segmentation procedures.

Figure 25:
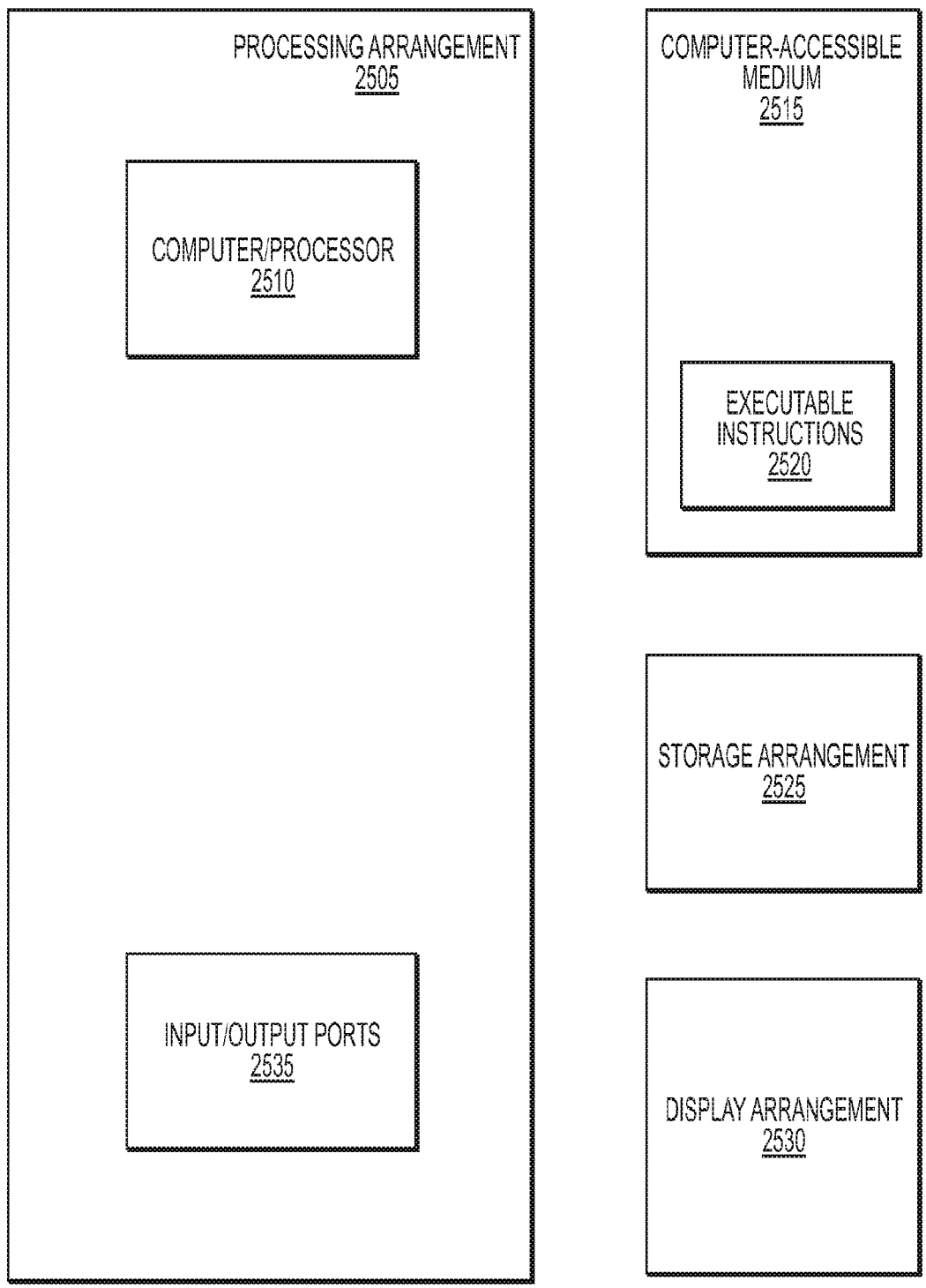
FIG. 25 is an illustration of an exemplary block diagram of an exemplary system in accordance with certain exemplary embodiments of the present disclosure.

FIG. 25 shows a block diagram of an exemplary embodiment of a system according to the present disclosure. For example, exemplary procedures in accordance with the present disclosure described herein can be performed by a processing arrangement and/or a computing arrangement 2505. Such processing/computing arrangement 2505 can be, for example entirely or a part of, or include, but not limited to, a computer/processor 2510 that can include, for example one or more microprocessors, and use instructions stored on a computer-accessible medium (e.g., RAM, ROM, hard drive, or other storage device).

As shown in FIG. 25, for example a computer-accessible medium 2515 (e.g., as described herein above, a storage device such as a hard disk, floppy disk, memory stick, CD-ROM, RAM, ROM, etc., or a collection thereof) can be provided (e.g., in communication with the processing arrangement 2505). The computer-accessible medium 2515 can contain executable instructions 2520 thereon. In addition or alternatively, a storage arrangement 2525 can be provided separately from the computer-accessible medium 2515, which can provide the instructions to the processing arrangement 2505 so as to configure the processing arrangement to execute certain exemplary procedures, processes and methods, as described herein above, for example.

Further, the exemplary processing arrangement 2505 can be provided with or include an input/output arrangement 2535, which can include, for example a wired network, a wireless network, the internet, an intranet, a data collection probe, a sensor, etc. As shown in FIG. 25, the exemplary processing arrangement 2505 can be in communication with an exemplary display arrangement 2530, which, according to certain exemplary embodiments of the present disclosure, can be a touch-screen configured for inputting information to the processing arrangement in addition to outputting information from the processing arrangement, for example. Further, the exemplary display 2530 and/or a storage arrangement 2525 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:
[1] Ian Goodfellow, Jean Pouget-Abadie, Mehdi Mirza, Bing Xu, David Warde-Farley, Sherjil Ozair, Aaron Courville, and Yoshua Bengio, Generative adversarial nets, Advances in neural information processing systems, 2014, pp. 2672-2680.
[2] Phillip Isola, Jun-Yan Zhu, Tinghui Zhou, and Alexei A Efros, Image-to-image translation with conditional adversarial networks, arXiv preprint arXiv:1611.07004 (2016).
[3] Alex Krizhevsky, Ilya Sutskever, and Geoffrey ∈Hinton, *Imagenet classification with deep convolutional neural*

*networks*, Advances in neural information processing systems, 2012, pp. 1097-1105.

What is claimed is:

1. A system for analyzing at least one anatomical structure of at least one patient,
the system configured to receive imaging information related to said at least one anatomical structure from at least one imaging device and comprising:
at least one core neural network trained first on classification procedures or segmentation procedures and then on segmentation procedures or classification procedures, said at least one core neural network to generate at least one feature of the at least one anatomical structure from the imaging information said at least one feature being useful at least for any of said classification and segmentation procedures; and
at least two classification and/or segmentation neural networks, each one to perform one of said multiple classification procedures and/or multiple segmentation procedures using at least said at least one feature to detect a portion of said at least one anatomical structure, to determine at least one anomaly of said at least one anatomical structure,
wherein at least one of said classification and/or segmentation neural networks also receives the output of a previous one of said neural networks.

2. The system of claim 1, wherein the imaging information includes at least three images of the at least one anatomical structure.

3. The system of claim 1, wherein the imaging information includes ultrasound imaging information.

4. The system of claim 1, wherein the at least one anatomical structure is a heart and wherein at least one classification neural network comprises:
a view detection neural network to detect a view of a particular imaging frame in the imaging information;
a systole/diastole detection neural network; and
an anomaly detection neural network;
and wherein said at least one segmentation neural network comprises:
a part segmentation neural network to segment parts of the heart of the at least one patient from a background; and
a valve localization neural network to localize a heart valve.

5. The system of claim 4, wherein an at least one state of said heart includes at least one of (i) a systole state of a heart of the at least one patient, (ii) a diastole state of the heart of the at least one patient, (iii) an inflation state of the heart of the at least one patient or (iv) a deflation state of the heart of the at least one patient.

6. The system of claim 4, and also comprising a unit to determine an ejection fraction using output of said view detection and part segmentation neural networks, where the segmentation neural network segments the left ventricle.

7. The system of claim 6, and also comprising a unit to place at least one Doppler measuring point within an appropriate view of said heart.

8. The system of claim 1, wherein the imaging information includes a plurality of images at different resolutions, and wherein the at least one neural network includes a plurality of neural networks, each of the neural networks being associated with one of the images.

9. A method for analyzing at least one anatomical structure of at least one patient, comprising:
training at least one core neural network first on multiple classification or multiple segmentation procedures and then on multiple segmentation or multiple classification procedures to generate features useful at least for any of said classification and segmentation procedures;
receiving imaging information related to the at least one anatomical structure of the at least one patient;
using said at least one core neural network, generating at least one feature of the at least one anatomical structure from the imaging information;
having at least two classification and/or segmentation neural networks; and
performing one of said multiple classification procedures with one of said classification neural networks and/or multiple segmentation procedures with one of said segmentation neural networks using at least said at least one feature to detect a portion of said at least one anatomical structure, to determine at least one anomaly or as input to a further procedure
wherein at least one of said classification and/or segmentation neural networks also receives the output of a previous one of said neural networks.

10. The method of claim 9, wherein the imaging information includes at least three images of the at least one anatomical structure.

11. The method of claim 9, wherein the imaging information includes ultrasound imaging information.

12. The method of claim 9, wherein the at least one anatomical structure is a heart and wherein at least one classification neural network comprises:
a view detection neural network to detect a view of a particular imaging frame in the imaging information;
a systole/diastole detection neural network; and
an anomaly detection neural network;
and wherein at least one segmentation neural network comprises:
a part segmentation neural network to segment parts of the heart of the at least one patient from a background; and
a valve localization neural network to localize a heart valve.

13. The method of claim 12, wherein an at least one state of said heart includes at least one of (i) a systole state of a heart of the at least one patient, (ii) a diastole state of the heart of the at least one patient, (iii) an inflation state of the heart of the at least one patient or (iv) a deflation state of the heart of the at least one patient.

14. The method of claim 12, and further comprising determining an ejection fraction using output of said view detection and part segmentation, where the segmentation neural network segments the left ventricle.

15. The method of claim 12, and further comprising placing at least one Doppler measuring point within an appropriate view of said heart.

16. The method of claim 9, wherein the imaging information includes a plurality of images at different resolutions, and wherein the at least one neural network includes a plurality of neural networks, each of the neural networks being associated with one of the images.

* * * * *